United States Patent [19]

Clough et al.

[11] Patent Number: 5,198,444
[45] Date of Patent: Mar. 30, 1993

[54] METHYL α-(2-SUBSTITUTED)PYRID-3-YL-β-METHOXYACRYLATES, COMPOSITIONS CONTAINING THEM AND THEIR USE AS FUNGICIDES

[75] Inventors: John M. Clough, Buckinghamshire; Christopher R. A. Godfrey; Stephen P. Heaney, both of Berkshire; Kenneth Anderton, Lancashire, all of England

[73] Assignee: Imperial Chemical Industries PLC, London, England

[21] Appl. No.: 597,398

[22] Filed: Oct. 15, 1990

Related U.S. Application Data

[63] Continuation of Ser. No. 258,742, Oct. 17, 1988, Pat. No. 5,008,276, which is a continuation-in-part of Ser. No. 39,401, Apr. 17, 1987, Pat. No. 4,826,531.

[30] Foreign Application Priority Data

Oct. 15, 1987 [GB] United Kingdom ............... 8724252

[51] Int. Cl.$^5$ ............... A01N 43/40; A01N 43/54; D07D 213/643; C07D 213/70
[52] U.S. Cl. ................... 514/269; 514/274; 514/335; 514/312; 514/357; 514/345; 514/256; 544/298; 544/333; 546/153; 546/261; 546/300; 546/301; 546/302
[58] Field of Search ............ 546/296, 297, 300, 301, 546/302, 261, 153; 514/345, 348, 349, 269, 335, 274, 312, 357, 256; 544/316, 319, 298, 333

[56] References Cited

U.S. PATENT DOCUMENTS

| 4,518,602 | 5/1985 | Terao et al. ............ 546/342 X |
| 4,772,633 | 9/1988 | Matsuo et al. .......... 546/290 X |
| 4,826,531 | 5/1989 | Anthony et al. ............ 71/94 |

FOREIGN PATENT DOCUMENTS

| 312221 | 4/1989 | European Pat. Off. ........... 546/301 |
| 2247399 | 4/1973 | Fed. Rep. of Germany ...... 546/290 |
| 60-193940 | 10/1985 | Japan ...................... 546/290 |

Primary Examiner—Mary C. Lee
Assistant Examiner—Lenora Ava Miltenberger
Attorney, Agent, or Firm—Cushman, Darby & Cushman

[57] ABSTRACT

Fungicidal compounds of the formula (I):

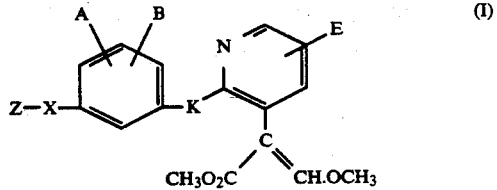

and stereoisomers thereof, wherein K is oxygen or sulphur; Z is optionally substituted aryl or optionally substituted heteroaryl; X is O, $S(O)_n$, $NR^4$, $CR^1R^2$, $CHR^5$, CO, $CR^1(OR^2)$, $C=CR^1R^2$, $CHR^1CHR^2$, $CR^1=CR^2$, $CHR^1CR^2=CH$, $C=C$, $OCHR^1$, $CHR^1O$, $OCHR^1O$, $S(O)_nCHR^1$, $S(O)_nCHR^1O$, $CHR^1S(O)_n$, $CHR^1OSO_2$, $NR^4CHR^1$, $CHR^1NR^4$, $CO_2$, $O_2C$, $SO_2O$, $OSO_2$, $CO.CO$, $COCHR^1$, $COCHR^1O$, $CHR^1CO$, $CHOH.CHR^1$, $CHR^1.CHOH$,

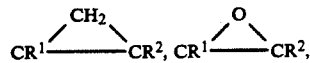

$CONR^4$, $OCONR^4$, $NR^4CO$, $CSNR^4$, $OCS.NR^4$, $SCO.NR^4$, $NR^4CO_2$, $NR^4CS$, $NR^4CSO$, $NR^4COS$, $NR^4CONR^4$, $S(O)_nNR^4$, $NR^4S(O)_n$, $CS_2$, $S_2C$, $CO.S$, $SCO$, $N=N$, $N=CR^1$, $CR^1=N$, $CHR^1CHR^2CH(OH)$, $CHR^1OCO$, $CHR^1SCO$, $CHR^1NR^4CO$, $CHR^1NR^4COR^4$, $CHR^1CHR^2CO$, $O.N=CR^1$, $CHR^1O.N=CR^2$, $CO.OCR^1R^2$, $CHR^1CHR^2CHR^3$, $OCHR^1CHR^2$, $(CH_2)_mO$, $CHR^1OCHR^2$, $CHR^1CHR^2O$, $OCHR^1CHR^2O$, $S(O)_nCHR^1CHR^2$, $CHR^1S(O)_nCHR^2$, $CHR^1CHR^2S(O)_n$, $CR^1=NNR^4$, $NR^4N=CR^1$, $CHR^1CONR^2$, $CHR^1OCO.NR^2$, $CH=CHCH_2O$, $COCHR^1CHR^2O$ or $(R^5)_2P+CHR^2Q^-$; A, B and E, which may be the same or different, are H, hydroxy, halo, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$, $R^2$ and $R^3$, which may be the same or different, are H, $C_{1-4}$ alkyl or phenyl; $R^4$ is H, $C_{1-4}$ alkyl or $COR^1$; $R^5$ is optionally substituted phenyl; $Q^-$ is a halide anion; n is 0, 1, or 2 and m is a 3, 4 or 5.

5 Claims, No Drawings

METHYL α-(2-SUBSTITUTED)PYRID-3-YL-β-METHOXYACRYLATES, COMPOSITIONS CONTAINING THEM AND THEIR USE AS FUNGICIDES

This is a continuation of application Ser. No. 07/258,742, filed Oct. 17, 1988, now U.S. Pat. No. 5,008,276 which is a continuation-in-part of Ser. No. 039,401, filed Apr. 17, 1987, now U.S. Pat. No. 4,826,531.

This invention relates to derivatives of propenoic acid useful as fungicides, to processes for preparing them, to fungicidal compositions containing them, and to methods of using them to combat fungi, especially fungal infections of plants.

The present invention provides a compound having the formula (I);

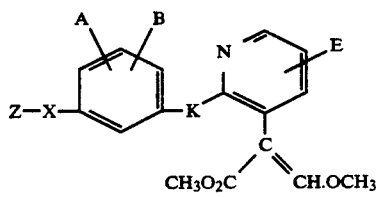

and stereoisomers thereof, wherein K is oxygen or sulphur; Z is optionally substituted aryl or optionally substituted heteroaryl; X is O, $S(O)_n$, $NR^4$, $CR^1R^2$, $CHR^5$, CO, $CR^1(OR^2)$, $C=CR^1R^2$, $CHR^1CHR^2$, $CR^1=CR^2$, $CHR^1CR^2=CH$, $C=C$, $OCHR^1$, $CHR^1O$, $OCHR^1O$, $S(O)_nCHR^1$, $S(O)_nCHR^1O$, $CHR^1S(O)_n$, $CHR^1OSO_2$, $NR^4CHR^1$, $CHR^1NR^4$, $CO_2$, $O_2C$, $SO_2O$, $OSO_2$, $CO.CO$, $COCHR^1$, $COCHR^1O$, $CHR^1CO$, $CHOH.CHR^1$, $CHR^1.CHOH$,

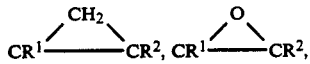

$CONR^4$, $OCONR^4$, $NR^4CO$, $CSNR^4$, $OCS.NR^4$, $SCO.NR^4$, $NR^4CO_2$, $NR^4CS$, $NR^4CSO$, $NR^4COS$, $NR^4CONR^4$, $S(O)_nNR^4$, $NR^4S(O)_n$, $CS_2$, $S_2C$, $CO.S$, $SCO$, $N=N$, $N=CR^1$, $CR^1=N$, $CHR^1CHR^2CH(OH)$, $CHR^1OCO$, $CHR^1SCO$, $CHR^1NR^4CO$, $CHR^1NR^4CONR^4$, $CHR^1CHR^2CO$, $O.N=CR^1$, $CHR^1O.N=CR^2$, $CO.OCR^1R^2$, $CHR^1CHR^2CHR^3$, $OCHR^1CHR^2$, $(CH_2)_mO$, $CHR^1OCHR^2$, $CHR^1CHR^2O$, $OCHR^1CHR^2O$, $S(O)_nCHR^1CHR^2$, $CHR^1S(O)_nCHR^2$, $CHR^1CHR^2S(O)_n$, $CR^1=NNR^4$, $NR^4N=CR^1$, $CHR^1CONR^2$, $CHR^1OCO.NR^2$, $CH=CHCH_2O$, $COCHR^1CHR^2O$, or $(R^5)_2P'CHR^2Q^-$; A, B and E, which may be the same or different are H, hydroxy, halo, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$, $R^2$ and $R^3$, which may be the same or different, are H, $C_{1-4}$ alkyl or phenyl; $R^4$ is H, $C_{1-4}$ alkyl or $COR^1$; $R^5$ is optionally substituted phenyl; $Q^-$ is a halide anion; n is 0, 1 or 2 and m is 3, 4 or 5.

Of particular interest are those compounds in which X is O, $OCH_2$, $CH_2O$, and $SO_2O$.

The compounds of the invention contain at least one carbon-carbon double bond, and are sometimes obtained in the form of mixtures of geometric isomers. However, these mixtures can be separated into individual isomers, and this invention embraces such isomers, and mixtures thereof in all proportions including those which consist substantially of the (Z)-isomer and those which consist substantially of the (E)-isomer.

The individual isomers which result from the unsymmetrically substituted double bond of the propenoate group are identified by the commonly used terms "E" and "Z". These terms are defined according to the Cahn-Ingold-Prelog system which is fully described in the literature (see, for example, J March, "Advanced Organic Chemistry", 3rd edition, Wiley-Interscience, page 109 et seq).

Usually one isomer is more active fungicidally than the other, the more active isomer usually being the one wherein the groups $-CO_2CH_3$ and $-OCH_3$ are on opposite sides of the olefinic bond of the propenoate group (the (E)-isomer). These (E)-isomers form a preferred embodiment of the invention.

The substituent Z in compound (I) is optionally substituted aryl or optionally substituted heteroaryl. Where valency allows, each of the optionally substituted groups aryl or heteroaryl can carry up to 5 substitutents. The term "aryl" includes phenyl in particular, and naphthyl. The term "heteroaryl" includes 5- and 6- membered heterocyclic groups containing one or more of each of the heteroatoms O, S and N (preferably S or N), fused benzenoid and heteroaromatic ring systems, and, in each case, the corresponding N-oxides. Examples of heteroaryl groups which Z may be are pyridinyl, pyrimidinyl, pyrazinyl, pyridazinyl, 1,2,3-, 1,2,4-, and 1,3,5-triazinyl, 1,2,4,5-tetrazinyl, 1,2,3- and 1,2,4-trizolyl, thienyl, furyl, pyrrolyl, thiazolyl, oxadiazolyl, quinolinyl, isoquinolinyl, quinoxalinyl, benzothienyl, benzoxazolyl and benzthiazolyl and, where appropriate, the corresponding N-oxides. Substituents which may be present in the optionally substituted aryl and heteroaryl moieties include one or more of the following; halo, hydroxy, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{2-4}$)alkyl (especially trifluoromethyl), halo($C_{1-4}$)alkoxy (especially trifluoromethoxy), $C_{1-4}$ alkylthio (especially methylthio), hydroxy($C_{1-4}$)alkyl, $C_{1-4}$alkoxy($C_{1-4}$)alkyl, $C_{3-6}$ cycloalkyl, $C_{3-6}$ cycloalkyl($C_{1-4}$)alkyl, optionally substituted aryl (especially optionally substituted phenyl), optionally substituted heteroaryl (especially optionally substituted pyridinyl or pyrimidinyl), optionally substituted aryloxy (especially optionally substituted phenoxy), optionally substituted heteroaryloxy (especially optionally substituted pyridinyloxy or pyrimidinyloxy), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$)alkyl (especially optionally substituted pyridinyl- or pyrimidinyl($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridinylethenyl or pyrimidinylethenyl), optionally substituted aryl($C_{1-4}$)alkoxy (especially optionally substituted benzyloxy), optionally substituted heteroaryl($C_{1-4}$)alkoxy (especially optionally substituted pyridinyl- or pyrimidinyl($C_{1-4}$)alkoxy), optionally substituted aryloxy($C_{1-4}$)alkyl (especially phenoxymethyl), optionally substituted heteroaryloxy($C_{1-4}$)alkyl (especially optionally substituted pyridinyloxy- or pyrimidinyloxy($C_{1-4}$)alkyl), acyloxy, including $C_{1-4}$ alkanoyloxy (especially acetyloxy) and benzoyloxy, cyano, thiocyanato, nitro, —NR'R'', —NHCOR'', —NHCONR'R'', —CONR'R'', —COOR', —OSO$_2$R', —SO$_2$R', —COR', —CR'=NR'' or —N=CR'R'' in which R' and R'' are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Substituents which may be present in the aryl or heteroaryl rings of any of the foregoing substituents and in the phenyl ring of $R^5$ include one or more of the following; halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$- alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzyloxy, cyano, thiocyanato, nitro, —NR'R'', —NHCOR', —NHCONR'R'', —CONR'R'', —COOR', —OSO$_2$R', —SO$_2$R', —COR', —CR'=NR'' or —N=CR'R'' in which R' and R'' have the meanings given above.

When any of the substituents A, B and E are $C_{1-4}$-alkyl or $C_{1-4}$ alkoxy, the alkyl moiety can be in the form of straight or branched chains, that is, the moiety may be methyl, ethyl, n- or iso-propyl, or n-, sec-, iso- or t-butyl. Other references herein to $C_{1-4}$ alkyl and $C_{1-4}$ alkoxy carry the same meaning. $C_{2-4}$ Alkenyl groups can be in the form of straight or branched chains and, where appropriate, may have either the (E)- or (Z)-configuration. Examples of such groups are vinyl, allyl, —C(CH$_3$):CH$_2$, and (E)- and (Z)-crotyl.

The substituents A and B are preferably in the 4- and 5-positions of the phenyl ring, and the substituent E is preferably a small group or a single atom such as hydrogen or halogen. Usually, E and one or both of A and B will be hydrogen.

In one aspect, the invention includes a compound having the formula (Ia):

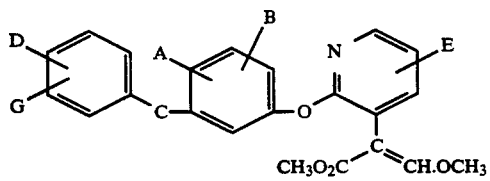

(Ia)

wherein X is O, S(O)$_n$ in which n is 0, 1 or 2, NH, NCH$_3$, NCH$_2$CH$_3$, NCOCH$_3$, NCH(CH$_3$)$_2$, CH$_2$, CH(CH$_3$), C(CH$_3$)$_2$, CO, C=CH$_2$, C=(CH$_3$)$_2$, CH$_2$CH$_2$, CH(CH$_3$)CH$_2$, CH$_2$CH(CH$_3$), (E)—CH=CH, (Z)—CH=CH, (E)—C(CH$_3$)=C(CH$_3$), C=C, OCH$_2$, OCH(CH$_3$), (CH$_2$)$_p$O in which p is an integer of 1 to 5, CH(CH$_3$)O, SCH$_2$, SCH(CH$_3$), S(O)CH$_2$, S(O)CH(CH$_3$), S(O)$_2$CH$_2$, S(O)$_2$CH(CH$_3$), CH$_2$S, CH(CH$_3$)S, CH$_2$S(O), CH(CH$_3$)S(O), CH$_2$S(O)$_2$, CH(CH$_3$)S(O)$_2$, NHCH$_2$, N(CH$_3$)CH$_2$, N(COCH$_3$)CH$_2$, NHCH(CH$_3$), N(CH$_3$)CH(CH$_3$), N(COCH$_3$)CH(CH$_3$), CH$_2$NH, CH$_2$N(CH$_3$), CH$_2$N(COCH$_3$), CH(CH$_3$)NH, CH(CH$_3$)N(CH$_3$), CH(CH$_3$)N(COCH$_3$), CO$_2$, O$_2$C, SO$_2$O, OSO$_2$, CO.CO, COCH$_2$, COCH(CH$_3$), CH$_2$CO, CH(CH$_3$)CO, CH(OH)CH$_2$, CH(OH)CH(CH$_3$), CH$_2$CH(OH), CH(CH$_3$)CH(OH), CONH, CON(CH$_3$), CON(CH$_2$CH$_2$CH$_3$), CON(CHO), CON(COCH$_3$), NHCO, N(CH$_3$)CO, N(CH$_2$CH$_3$)CO, N(CHO)CO, N(COCH$_3$)CO, CSN(CH$_3$), CSNH, NHCS, N(CH$_3$)CS, SO$_2$NH, SO$_2$N(CH$_3$), NHSO$_2$, N(CH$_3$)SO$_2$, N(CH$_2$CH$_3$)SO$_2$, CS$_2$, S$_2$C, COS, SCO, (E)—N=N, (E)—N=CH, (E)—N=C(CH$_3$), (E)—CH$_2$=N, (E)—C(CH$_3$)=N, CH$_2$CH$_2$CH$_2$, CH(CH$_3$)CH$_2$CH$_2$, CH$_2$CH(CH$_3$)CH$_2$, CH$_2$CH$_2$CH(CH$_3$), OCH$_2$CH$_2$, CH$_2$OCH$_2$, SCH$_2$CH$_2$, S(O)CH$_2$CH$_2$, S(O)$_2$CH$_2$CH$_2$, CH$_2$SCH$_2$, CH$_2$S(O)CH$_2$, CH$_2$S(O)$_2$CH$_2$, CH$_2$CH$_2$S, CH$_2$CH$_2$S(O), CH$_2$CH$_2$S(O)$_2$, (E)—CH=NNH, (E)—C(CH$_2$)=NNH, (E)—CH=NN(CH$_3$), (E)—NHN=CH, (E)—NHN=C(CH$_3$), (E)—N(CH$_3$)N=CH, CH$_2$CONH, CH(CH$_3$)CON(CH$_3$), (E)—CH=CHCH$_2$O, COCH$_2$CH$_2$O,

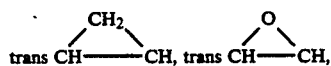

CH(C$_6$H$_5$), COCH$_2$O, CH(OH), CO$_2$CH$_2$, (C$_6$H$_5$)$_2$P$^+$CH$_2$Br$^-$, CH$_2$OCO, CH$_2$NHCO, CH$_2$SCO, OCH$_2$O, OCH$_2$CH$_2$O, S(O)CH$_2$O, COCH(CH$_3$)O, (E)—CH$_2$ON=CH, (Z)—CH$_2$ON=CH, CH$_2$CH$_2$CH(OH), (E)—CH$_2$CH=CH, C(CH$_3$)(OH), CH$_2$OSO$_2$, CH$_2$NHCO.NH, OCO.NH, NHCO.NH or CH$_2$OCO.NH, A is H, hydroxy, halo, $C_{1-4}$ alkyl, $C_{1-4}$ alkoxy, trifluoromethyl, nitro, cyano, acetyl or phenoxy; B and E are H or halo; D is H, hydroxy, halo, $C_{1-4}$ alkyl, $C_{1-4}$ alkoxy, nitro, cyano, halo($C_{1-4}$)alkyl (especially trifluoromethyl), halo($C_{1-4}$)alkoxy (especially trifluoro-methoxy), phenyl, phenoxy, NHCOR$^6$, NHSO$_2$R$^6$, NR$^7$R$^8$, CO$_2$R$^7$, wherein R$^6$ is $C_{1-4}$ alkyl (especially methyl) or phenyl and R$^7$ and R$^8$ are independently H or $C_{1-4}$ alkyl, or CH$_3$O$_2$C.C=CH.OCH$_3$; and G is H, halo, $C_{1-4}$ alkyl, $C_{1-4}$ alkoxy or nitro; or D and G, when they are adjacent, join to form a benzene or pyridine ring.

More particularly, it includes a compound having the formula (Ia) wherein X is O, OCH$_2$, CH$_2$O, CH(OH) or SO$_2$O; A is H, hydroxy, halo, $C_{1-4}$ alkyl, $C_{1-4}$ alkoxy, trifluoromethyl, nitro, cyano, acetyl or phenoxy; B and E are H or halo; D is H, hydroxy, halo, $C_{1-4}$ alkyl, $C_{1-4}$ alkoxy, nitro, cyano, halo($C_{1-4}$)alkyl (especially trifluoromethyl), halo($C_{1-4}$)alkoxy (especially trifluoromethoxy), phenyl, phenoxy, NHCOR$^6$, NHSO$_2$R$^6$, NR$^7$R$^8$ or CO$_2$R$^7$, wherein R$^6$ is $C_{1-4}$ alkyl (especially methyl) or phenyl and R$^7$ and R$^8$ are independently H or $C_{1-4}$ alkyl; and G is H, halo, $C_{1-4}$ alkyl, $C_{1-4}$ alkoxy or nitro. Of special interest are compounds of the formula (Ia) wherein X is O, OCH$_2$, CH$_2$O or SO$_2$O,; D is H, halo, $C_{1-4}$ alkyl, $C_{1-4}$ alkoxy, nitro, cyano or amino; and A, B, E and G are all H.

In another aspect, the invention includes a compound having the formula (Ib):

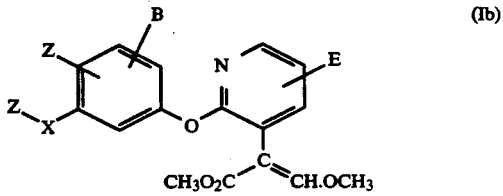

(Ib)

wherein Z is pyridinyl, pyrimidinyl, triazinyl, pyrazinyl, pyridazinyl, quinolinyl, benzoxazolyl, benzthiazolyl, thienyl, quinoxalinyl, thiazolyl, isoquinolinyl, quinazolinyl, purinyl, oxazolyl, thiadiazolyl, oxadiazolyl, furyl, pyrrolyl or thienopyrimidinyl, each optionally substituted with halo, $C_{1-4}$ alkyl, $C_{1-4}$ alkoxy, $C_{1-4}$ alkylthio, halo($C_{1-4}$)alkyl (especially trifluoromethyl), cyano, nitro, $SO_2R^6$, $COOR^7$, phenyl, phenoxy, $C_{1-4}$ alkanoyl and $CONR^7R^8$ in which $R^6$ is $C_{1-4}$ alkyl and $R^7$ and $R^8$ are independently H or $C_{1-4}$ alkyl, and N-oxides thereof; X is O, S, NH, N($CH_3$), $SO_2O$, $CH_2$, $CH_2CH_2$, $OCH_2$, $CH_2O$, CH(OH), CONH or CO; A and B are independently H, halo, $C_{1-4}$ alkyl, $C_{1-4}$ alkoxy, cyano, nitro, halo($C_{1-4}$)alkyl (especially trifluoromethyl) or halo($C_{1-4}$)alkoxy (especially trifluoromethoxy); and E is H or halo.

More particularly, it includes a compound having the formula (Ib) wherein X is O, $OCH_2$, $CH_2O$, CH(OH) or $SO_2O$; Z is pyridinyl, pyrimidinyl or thiazolyl, each optionally substituted with halo, $C_{1-4}$ alkyl, $C_{1-4}$ alkoxy, $C_{1-4}$ alkylthio, halo($C_{1-4}$)alkyl (especially trifluoromethyl), cyano, nitro, $SO_2R^6$, $COOR^7$, phenyl, phenoxy, $C_{1-4}$ alkanoyl and $CONR^7R^8$ in which $R^6$ is $C_{1-4}$ alkyl and $R^7$ and $R^8$ are independently H or $C_{1-4}$ alkyl, and N-oxides thereof; A and B are independently H, halo, $C_{1-4}$ alkyl, $C_{1-4}$ alkoxy, cyano, nitro, halo($C_{1-4}$)alkyl (especially trifluoromethyl) or halo($C_{1-4}$)alkoxy (especially trifluoromethoxy); and E is H or halo.

Of special interest are compounds of the formula (Ib) wherein X is O or $OCH_2$; Z is pyridin-2-yl, pyrimidin-2-yl, pyrimidin-4-yl or thiazol-2-yl each optionally substituted with halogen, cyano, nitro or $SO_2R^6$ in which $R^6$ is $C_{1-4}$ alkyl; and A, B and E are all H.

In yet another aspect, the invention includes a compound having the formula (Ic):

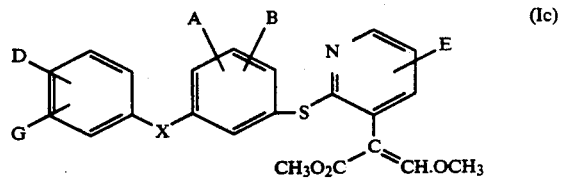

(Ic)

wherein X, A, B, D, E and G have the meanings given for the compound (Ia).

In still yet another aspect, the invention includes a compound having the formula (Id):

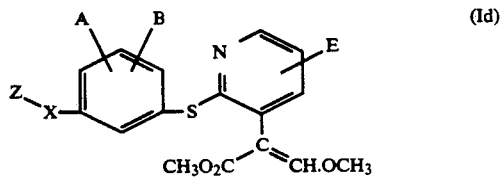

(Id)

wherein Z, X, A, B and E have the meanings given for the compound (Ib).

The invention is illustrated by the compounds listed in Tables I, II, III and IV which follow. Throughout Tables I, II, III and IV the methyl 3-methoxypropenoate group has the (E)-configuration.

TABLE I

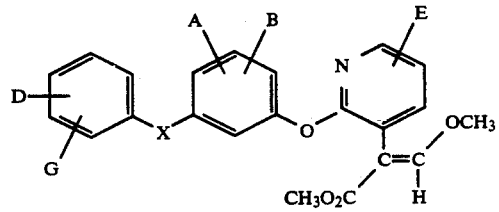

| Compound No. | X | D | G | A | B | E | Olefinic+ | Melting Point (°C.) |
|---|---|---|---|---|---|---|---|---|
| 1 | S | H | H | H | H | H | | |
| 2 | SO | H | H | H | H | H | | |
| 3 | $SO_2$ | H | H | H | H | H | | |
| 4 | NH | H | H | H | H | H | | |
| 5 | $NCH_3$ | H | H | H | H | H | | |
| 6 | $NCH_2CH_3$ | H | H | H | H | H | | |
| 7 | $NCOCH_3$ | H | H | H | H | H | | |
| 8 | $NCH(CH_3)_2$ | H | H | H | H | H | | |
| 9 | $CH_2$ | H | H | H | H | H | | |
| 10 | $CH(CH_3)$ | H | H | H | H | H | | |
| 11 | $C(CH_3)_2$ | H | H | H | H | H | | |
| 12 | CO | H | H | H | H | H | | |
| 13 | $C:CH_2$ | H | H | H | H | H | | |
| 14 | $C:C(CH_3)_2$ | H | H | H | H | H | | |
| 15 | $CH_2CH_2$ | H | H | H | H | H | | |
| 16 | $CH(CH_3)CH_2$ | H | H | H | H | H | | |
| 17 | $CH_2CH(CH_3)$ | H | H | H | H | H | | |
| 18 | (E)—CH:CH | H | H | H | H | H | | |
| 19 | (E)—$C(CH_3):C(CH_3)$ | H | H | H | H | H | | |
| 20 | C:C | H | H | H | H | H | 7.58 | Gum |
| 21 | $OCH_2$ | H | H | H | H | H | | |
| 22 | $OCH(CH_3)$ | H | H | H | H | H | 7.58 | 119–122 |
| 23 | $CH_2O$ | H | H | H | H | H | | |
| 24 | $CH(CH_3)O$ | H | H | H | H | H | | |
| 25 | $SCH_2$ | H | H | H | H | H | | |
| 26 | $SCH(CH_3)$ | H | H | H | H | H | | |
| 27 | $S(O)CH_2$ | H | H | H | H | H | | |
| 28 | $S(O)CH(CH_3)$ | H | H | H | H | H | | |
| 29 | $S(O)_2CH_2$ | H | H | H | H | H | | |
| 30 | $S(O)_2CH(CH_3)$ | H | H | H | H | H | | |

TABLE I-continued

| | | | | | | |
|---|---|---|---|---|---|---|
| 31 | CH₂S | H | H | H | H | H |
| 32 | CH(CH₃)S | H | H | H | H | H |
| 33 | CH₂S(O) | H | H | H | H | H |
| 34 | CH(CH₃)S(O) | H | H | H | H | H |
| 35 | CH₂S(O)₂ | H | H | H | H | H |
| 36 | CH(CH₃)S(O)₂ | H | H | H | H | H |
| 37 | NHCH₂ | H | H | H | H | H |
| 38 | N(CH₃)CH₂ | H | H | H | H | H |
| 39 | N(COCH₃)CH₂ | H | H | H | H | H |
| 40 | NHCH(CH₃) | H | H | H | H | H |
| 41 | N(CH₃)CH(CH₃) | H | H | H | H | H |
| 42 | N(COCH₃)CH(CH₃) | H | H | H | H | H |
| 43 | CH₂NH | H | H | H | H | H |
| 44 | CH₂N(CH₃) | H | H | H | H | H |
| 45 | CH₂N(COCH₃) | H | H | H | H | H |
| 46 | CH(CH₃)NH | H | H | H | H | H |
| 47 | CH(CH₃)N(CH₃) | H | H | H | H | H |
| 48 | CH(CH₃)N(COCH₃) | H | H | H | H | H |
| 49 | CO₂ | H | H | H | H | H |
| 50 | O₂C | H | H | H | H | H |
| 51 | SO₂O | H | H | H | H | H |
| 52 | OSO₂ | H | H | H | H | H |
| 53 | CO.CO | H | H | H | H | H |
| 54 | COCH₂ | H | H | H | H | H |
| 55 | COCH(CH₃) | H | H | H | H | H |
| 56 | CH₂CO | H | H | H | H | H |
| 57 | CH(CH₃)CO | H | H | H | H | H |
| 58 | CH(OH)CH₂ | H | H | H | H | H |
| 59 | CH(OH)CH(CH₃) | H | H | H | H | H |
| 60 | CH₂CH(OH) | H | H | H | H | H |
| 61 | CH(CH₃)CH(OH) | H | H | H | H | H |
| 62 | CONH | H | H | H | H | H |
| 63 | CON(CH₃) | H | H | H | H | H |
| 64 | CON(CH₂CH₂CH₃) | H | H | H | H | H |
| 65 | CON(CHO) | H | H | H | H | H |
| 66 | CON(COCH₃) | H | H | H | H | H |
| 67 | NHCO | H | H | H | H | H |
| 68 | N(CH₃)CO | H | H | H | H | H |
| 69 | N(CH₂CH₃)CO | H | H | H | H | H |
| 70 | N(CHO)CO | H | H | H | H | H |
| 71 | N(COCH₃)CO | H | H | H | H | H |
| 72 | CSN(CH₃) | H | H | H | H | H |
| 73 | CSNH | H | H | H | H | H |
| 74 | NHCS | H | H | H | H | H |
| 75 | N(CH₃)CS | H | H | H | H | H |
| 76 | SO₂NH | H | H | H | H | H |
| 77 | SO₂N(CH₃) | H | H | H | H | H |
| 78 | NHSO₂ | H | H | H | H | H |
| 79 | N(CH₃)SO₂ | H | H | H | H | H |
| 80 | N(CH₂CH₃)SO₂ | H | H | H | H | H |
| 81 | CS₂ | H | H | H | H | H |
| 82 | S₂C | H | H | H | H | H |
| 83 | COS | H | H | H | H | H |
| 84 | SCO | H | H | H | H | H |
| 85 | (E)—N:N | H | H | H | H | H |
| 86 | (E)—N:CH | H | H | H | H | H |
| 87 | (E)—N:C(CH₃) | H | H | H | H | H |
| 88 | (E)—CH:N | H | H | H | H | H |
| 89 | (E)—C(CH₃):N | H | H | H | H | H |
| 90 | CH₂CH₂CH₂ | H | H | H | H | H |
| 91 | CH(CH₃)CH₂CH₂ | H | H | H | H | H |
| 92 | CH₂CH(CH₃)CH₂ | H | H | H | H | H |
| 93 | CH₂CH₂CH(CH₃) | H | H | H | H | H |
| 94 | OCH₂CH₂ | H | H | H | H | H |
| 95 | CH₂OCH₂ | H | H | H | H | H |
| 96 | CH₂CH₂O | H | H | H | H | H |
| 97 | SCH₂CH₂ | H | H | H | H | H |
| 98 | S(O)CH₂CH₂ | H | H | H | H | H |
| 99 | S(O)₂CH₂CH₂ | H | H | H | H | H |
| 100 | CH₂SCH₂ | H | H | H | H | H |
| 101 | CH₂S(O)CH₂ | H | H | H | H | H |
| 102 | CH₂S(O)₂CH₂ | H | H | H | H | H |
| 103 | CH₂CH₂S | H | H | H | H | H |
| 104 | CH₂CH₂S(O) | H | H | H | H | H |
| 105 | CH₂CH₂S(O)₂ | H | H | H | H | H |
| 106 | (E)—CH:NNH | H | H | H | H | H |
| 107 | (E)—C(CH₃):NNH | H | H | H | H | H |
| 108 | (E)—CH:NN(CH₃) | H | H | H | H | H |
| 109 | (E)—NHN:CH | H | H | H | H | H |
| 110 | (E)—NHN:C(CH₃) | H | H | H | H | H |
| 111 | (E)—N(CH₃)N:CH | H | H | H | H | H |
| 112 | CH₂CONH | H | H | H | H | H |

TABLE I-continued

| | | | | | | | | |
|---|---|---|---|---|---|---|---|---|
| 113 | CH(CH₃)CON(CH₃) | H | H | H | H | H | | |
| 114 | CH(CH₃)CON(CH₃) | H | H | H | H | H | | |
| 115 | (E)—CH:CHCH₂O | H | H | H | H | H | | |
| 116 | COCH₂CH₂O | H | H | H | H | H | | |
| 117 | trans CH—CH (CH₂) | H | H | H | H | H | | |
| 118 | trans CH—CH (O) | H | H | H | H | H | | |
| 119 | O | 2-Cl | H | H | H | H | 7.57 | 88-9 |
| 120 | O | 3-Cl | H | H | H | H | | |
| 121 | O | 4-Cl | H | H | H | H | | |
| 122 | O | 2-F | H | H | H | H | | |
| 123 | O | 3-F | H | H | H | H | | |
| 124 | O | 4-F | H | H | H | H | | |
| 125 | O | 2-CH₃ | H | H | H | H | | |
| 126 | O | 3-CH₃ | H | H | H | H | | |
| 127 | O | 4-CH₃ | H | H | H | H | | |
| 128 | O | 2-CH₃O | H | H | H | H | 7.57 | Gum |
| 129 | O | 3-CH₃O | H | H | H | H | | |
| 130 | O | 4-CH₃O | H | H | H | H | | |
| 131 | O | 2-NO₂ | H | H | H | H | 7.58 | 99-100 |
| 132 | O | 3-NO₂ | H | H | H | H | | |
| 133 | O | 4-NO₂ | H | H | H | H | 7.59 | 102-103 |
| 134 | O | 2-CN | H | H | H | H | 7.58 | Gum |
| 135 | O | 3-CN | H | H | H | H | | |
| 136 | O | 4-CN | H | H | H | H | | |
| 137 | O | 2-Br | H | H | H | H | | |
| 138 | O | 3-Br | H | H | H | H | | |
| 139 | O | 4-Br | H | H | H | H | | |
| 140 | O | 2-CF₃ | H | H | H | H | | |
| 141 | O | 3-CF₃ | H | H | H | H | | |
| 142 | O | 4-CF₃ | H | H | H | H | | |
| 143 | O | 2-C₆H₅O | H | H | H | H | | |
| 144 | O | 3-C₆H₅O | H | H | H | H | | |
| 145 | O | 4-C₆H₅O | H | H | H | H | | |
| 146 | O | 2-CH₃CH₂O | H | H | H | H | | |
| 147 | O | 3-CH₃CH₂O | H | H | H | H | | |
| 148 | O | 4-CH₃CH₂O | H | H | H | H | | |
| 149 | O | 2-C₂H₅ | H | H | H | H | | |
| 150 | O | 3-C₆H₅ | H | H | H | H | | |
| 151 | O | 4-C₆H₅ | H | H | H | H | | |
| 152 | O | 2-Cl | 3-Cl | H | H | H | | |
| 153 | O | 2-Cl | 4-Cl | H | H | H | | |
| 154 | O | 2-Cl | 5-Cl | H | H | H | | |
| 155 | O | 2-Cl | 6-Cl | H | H | H | | |
| 156 | O | 3-Cl | 4-Cl | H | H | H | | |
| 157 | O | 3-Cl | 5-Cl | H | H | H | | |
| 158 | O | 2-Cl | 3-CH₃O | H | H | H | | |
| 159 | O | 2-Cl | 4-CH₃O | H | H | H | | |
| 160 | O | 2-Cl | 5-CH₃O | H | H | H | | |
| 161 | O | 2-Cl | 6-CH₃O | H | H | H | | |
| 162 | O | 3-Cl | 4-CH₃O | H | H | H | | |
| 163 | O | 3-Cl | 5-CH₃O | H | H | H | | |
| 164 | O | 2-CH₃O | 3-Cl | H | H | H | | |
| 165 | O | 2-CH₃O | 4-Cl | H | H | H | | |
| 166 | O | 2-CH₃O | 5-Cl | H | H | H | | |
| 167 | O | 3-CH₃O | 4-Cl | H | H | H | | |
| 168 | O | | | H | H | H | | |
| 169 | O | | | H | H | H | | |
| 170 | O | H | H | 2-F | H | H | | |
| 171 | O | H | H | 4-F | H | H | | |
| 172 | O | H | H | 5-F | H | H | | |
| 173 | O | H | H | 6-F | H | H | | |
| 174 | O | H | H | 4-Cl | H | H | | |
| 175 | O | H | H | 5-Cl | H | H | | |
| 176 | O | H | H | 4-CH₃ | H | H | | |
| 177 | O | H | H | 5-CH₃ | H | H | | |
| 178 | O | H | H | 4-CH₃O | H | H | | |
| 179 | O | H | H | 5-CH₃O | H | H | | |
| 180 | O | H | H | 4-Br | H | H | | |
| 181 | O | H | H | 5-Br | H | H | | |
| 182 | O | H | H | 4-CF₃ | H | H | | |
| 183 | O | H | H | 5-CF₃ | H | H | | |
| 184 | O | H | H | 4-NO₂ | H | H | | |
| 185 | O | H | H | 5-NO₂ | H | H | | |
| 186 | O | H | H | 4-CN | H | H | | |
| 187 | O | H | H | 5-CN | H | H | | |
| 188 | O | H | H | 4-F | 5-F | H | | |

TABLE I-continued

| | | | | | | | | |
|---|---|---|---|---|---|---|---|---|
| 189 | O | H | H | 4-Cl | 5-Cl | H | | |
| 190 | O | H | H | 4-F | 5-Cl | H | | |
| 191 | O | H | H | 4-Cl | 5-F | H | | |
| 192 | O | H | H | 4-CH$_3$O | 5-Cl | H | | |
| 193 | O | H | H | 4-CH$_3$O | 5-F | H | | |
| 194 | O | H | H | H | H | 5-F | | |
| 195 | O | H | H | H | H | 6-Cl | | |
| 196 | (E)—N:N | H | H | 4-CH$_3$O | H | H | | |
| 197 | (E)—N:N | H | H | 4-CH$_3$CH$_2$O | H | H | | |
| 198 | CH$_2$O | 2-Cl | H | H | H | H | | |
| 199 | CH$_2$O | 3-Cl | H | H | H | H | | |
| 200 | CH$_2$O | 4-Cl | H | H | H | H | | |
| 201 | CH$_2$O | 2-F | H | H | H | H | | |
| 202 | CH$_2$O | 3-F | H | H | H | H | | |
| 203 | CH$_2$O | 4-F | H | H | H | H | | |
| 204 | CH$_2$O | 2-CH$_3$ | H | H | H | H | | |
| 205 | CH$_2$O | 3-CH$_3$ | H | H | H | H | | |
| 206 | CH$_2$O | 4-CH$_3$ | H | H | H | H | | |
| 207 | CH$_2$O | 2-CH$_3$O | H | H | H | H | | |
| 208 | CH$_2$O | 3-CH$_3$O | H | H | H | H | | |
| 209 | CH$_2$O | 4-CH$_3$O | H | H | H | H | | |
| 210 | CH$_2$O | 2-NO$_2$ | H | H | H | H | | |
| 211 | CH$_2$O | 3-NO$_2$ | H | H | H | H | | |
| 212 | CH$_2$O | 4-NO$_2$ | H | H | H | H | 7.58 | 125–127 |
| 213 | CH$_2$O | 2-CN | H | H | H | H | | |
| 214 | CH$_2$O | 3-CN | H | H | H | H | | |
| 215 | CH$_2$O | 4-CN | H | H | H | H | | |
| 216 | CH$_2$O | 2-Br | H | H | H | H | | |
| 217 | CH$_2$O | 3-Br | H | H | H | H | | |
| 218 | CH$_2$O | 4-Br | H | H | H | H | | |
| 219 | CH$_2$O | 2-CF$_3$ | H | H | H | H | | |
| 220 | CH$_2$O | 3-CF$_3$ | H | H | H | H | | |
| 221 | CH$_2$O | 4-CF$_3$ | H | H | H | H | | |
| 222 | CH$_2$O | 2-C$_6$H$_5$O | H | H | H | H | | |
| 223 | CH$_2$O | 3-C$_6$H$_5$O | H | H | H | H | | |
| 224 | CH$_2$O | 4-C$_6$H$_5$O | H | H | H | H | | |
| 225 | CH$_2$O | 2-CH$_3$CH$_2$O | H | H | H | H | | |
| 226 | CH$_2$O | 3-CH$_3$CH$_2$O | H | H | H | H | | |
| 227 | CH$_2$O | 4-CH$_3$CH$_2$O | H | H | H | H | | |
| 228 | CH$_2$O | 2-C$_6$H$_5$ | H | H | H | H | | |
| 229 | CH$_2$O | 3-C$_6$H$_5$ | H | H | H | H | | |
| 230 | CH$_2$O | 4-C$_6$H$_5$ | H | H | H | H | | |
| 231 | CH$_2$O | 2-Cl | 3-Cl | H | H | H | | |
| 232 | CH$_2$O | 2-Cl | 4-Cl | H | H | H | | |
| 233 | CH$_2$O | 2-Cl | 5-Cl | H | H | H | | |
| 234 | CH$_2$O | 2-Cl | 6-Cl | H | H | H | | |
| 235 | CH$_2$O | 3-Cl | 4-Cl | H | H | H | | |
| 236 | CH$_2$O | 3-Cl | 5-Cl | H | H | H | | |
| 237 | CH$_2$O | 2-Cl | 3-CH$_3$O | H | H | H | | |
| 238 | CH$_2$O | 2-Cl | 4-CH$_3$O | H | H | H | | |
| 239 | CH$_2$O | 2-Cl | 5-CH$_3$O | H | H | H | | |
| 240 | CH$_2$O | 2-Cl | 6-CH$_3$O | H | H | H | | |
| 241 | CH$_2$O | 3-Cl | 4-CH$_3$O | H | H | H | | |
| 242 | CH$_2$O | 3-Cl | 5-CH$_3$O | H | H | H | | |
| 243 | CH$_2$O | 2-CH$_3$O | 3-Cl | H | H | H | | |
| 244 | CH$_2$O | 2-CH$_3$O | 4-Cl | H | H | H | | |
| 245 | CH$_2$O | 2-CH$_3$O | 5-Cl | H | H | H | | |
| 246 | CH$_2$O | 3-CH$_3$O | 4-Cl | H | H | H | | |
| 247 | CH$_2$O | | | H | H | H | | |
| 248 | CH$_2$O | | | H | H | H | | |
| 249 | CH$_2$O | H | H | 2-F | H | H | | |
| 250 | CH$_2$O | H | H | 4-F | H | H | | |
| 251 | CH$_2$O | H | H | 5-F | H | H | | |
| 252 | CH$_2$O | H | H | 6-F | H | H | | |
| 253 | CH$_2$O | H | H | 4-Cl | H | H | | |
| 254 | CH$_2$O | H | H | 5-Cl | H | H | | |
| 255 | CH$_2$O | H | H | 4-CH$_3$ | H | H | | |
| 256 | CH$_2$O | H | H | 5-CH$_3$ | H | H | | |
| 257 | CH$_2$O | H | H | 4-CH$_3$O | H | H | | |
| 258 | CH$_2$O | H | H | 5-CH$_3$O | H | H | | |
| 259 | CH$_2$O | H | H | 4-Br | H | H | | |
| 260 | CH$_2$O | H | H | 5-Br | H | H | | |
| 261 | CH$_2$O | H | H | 4-CF$_3$ | H | H | | |
| 262 | CH$_2$O | H | H | 5-CF$_3$ | H | H | | |
| 263 | CH$_2$O | H | H | 4-NO$_2$ | H | H | | |
| 264 | CH$_2$O | H | H | 5-NO$_2$ | H | H | | |
| 265 | CH$_2$O | H | H | 4-CN | H | H | | |
| 266 | CH$_2$O | H | H | 5-CN | H | H | | |
| 267 | CH$_2$O | H | H | 4-F | 5-F | H | | |
| 268 | CH$_2$O | H | H | 4-Cl | 5-Cl | H | | |
| 269 | CH$_2$O | H | H | 4-F | 5-Cl | H | | |
| 270 | CH$_2$O | H | H | 4-Cl | 5-F | H | | |

TABLE I-continued

| | | | | | | | |
|---|---|---|---|---|---|---|---|
| 271 | CH₂O | H | H | 4-CH₃O | 5-Cl | H | |
| 272 | CH₂O | H | H | 4-CH₃O | 5-F | H | |
| 273 | CH₂O | H | H | H | H | 5-F | |
| 274 | CH₂O | H | H | H | H | 6-Cl | |
| 275 | O | 4-NH.COCH₃ | H | H | H | H | |
| 276 | O | 4-NH.SO₂C₆H₅ | H | H | H | H | |
| 277 | O | 4-NH.COC₆H₅ | H | H | H | H | |
| 278 | O | 4-NH.SO₂CH₃ | H | H | H | H | |
| 279 | O | 4-N(CH₃)₂ | H | H | H | H | |
| 280 | SO₂O | 4-NH.COCH₃ | H | H | H | H | |
| 281 | SO₂O | 3-NO₂ | 4-Cl | H | H | H | |
| 282 | (E)—N:N | 4-Cl | H | 4-HO | H | H | |
| 283 | SO₂O | 2-Cl | H | H | H | H | |
| 284 | SO₂O | 3-Cl | H | H | H | H | |
| 285 | SO₂O | 4-Cl | H | H | H | H | |
| 286 | SO₂O | 2-F | H | H | H | H | |
| 287 | SO₂O | 3-F | H | H | H | H | |
| 288 | SO₂O | 4-F | H | H | H | H | |
| 289 | SO₂O | 2-CH₃ | H | H | H | H | |
| 290 | SO₂O | 3-CH₃ | H | H | H | H | |
| 291 | SO₂O | 4-CH₃ | H | H | H | H | |
| 292 | SO₂O | 2-CH₃O | H | H | H | H | |
| 293 | SO₂O | 3-CH₃O | H | H | H | H | |
| 294 | SO₂O | 4-CH₃O | H | H | H | H | |
| 295 | SO₂O | 2-NO₂ | H | H | H | H | |
| 296 | SO₂O | 3-NO₂ | H | H | H | H | 7.57 49–51 |
| 297 | SO₂O | 4-NO₂ | H | H | H | H | |
| 298 | SO₂O | 2-CN | H | H | H | H | |
| 299 | SO₂O | 3-CN | H | H | H | H | |
| 300 | SO₂O | 4-CN | H | H | H | H | |
| 301 | SO₂O | 2-Br | H | H | H | H | |
| 302 | SO₂O | 3-Br | H | H | H | H | |
| 303 | SO₂O | 4-Br | H | H | H | H | |
| 304 | SO₂O | 2-CF₃ | H | H | H | H | |
| 305 | SO₂O | 3-CF₃ | H | H | H | H | |
| 306 | SO₂O | 4-CF₃ | H | H | H | H | |
| 307 | SO₂O | 2-C₆H₅O | H | H | H | H | |
| 308 | SO₂O | 3-C₆H₅O | H | H | H | H | |
| 309 | SO₂O | 4-C₆H₅O | H | H | H | H | |
| 310 | SO₂O | 2-CH₃CH₂O | H | H | H | H | |
| 311 | SO₂O | 3-CH₃CH₂O | H | H | H | H | |
| 312 | SO₂O | 4-CH₃CH₂O | H | H | H | H | |
| 313 | SO₂O | 2-C₆H₅ | H | H | H | H | |
| 314 | SO₂O | 3-C₆H₅ | H | H | H | H | |
| 315 | SO₂O | 4-C₆H₅ | H | H | H | H | |
| 316 | SO₂O | 2-Cl | 3-Cl | H | H | H | |
| 317 | SO₂O | 2-Cl | 4-Cl | H | H | H | |
| 318 | SO₂O | 2-Cl | 5-Cl | H | H | H | |
| 319 | SO₂O | 2-Cl | 6-Cl | H | H | H | |
| 320 | SO₂O | 3-Cl | 4-Cl | H | H | H | |
| 321 | SO₂O | 3-Cl | 5-Cl | H | H | H | |
| 322 | SO₂O | 2-Cl | 3-CH₃O | H | H | H | |
| 323 | SO₂O | 2-Cl | 4-CH₃O | H | H | H | |
| 324 | SO₂O | 2-Cl | 5-CH₃O | H | H | H | |
| 325 | SO₂O | 2-Cl | 6-CH₃O | H | H | H | |
| 326 | SO₂O | 3-Cl | 4-CH₃O | H | H | H | |
| 327 | SO₂O | 3-Cl | 5-CH₃O | H | H | H | |
| 328 | SO₂O | 2-CH₃O | 3-Cl | H | H | H | |
| 329 | SO₂O | 2-CH₃O | 4-Cl | H | H | H | |
| 330 | SO₂O | 2-CH₃O | 5-Cl | H | H | H | |
| 331 | SO₂O | 3-CH₃O | 4-Cl | H | H | H | |
| 332 | SO₂O | | | H | H | H | |
| 333 | SO₂O | | | H | H | H | |
| 334 | SO₂O | H | H | 2-F | H | H | |
| 335 | SO₂O | H | H | 4-F | H | H | |
| 336 | SO₂O | H | H | 5-F | H | H | |
| 337 | SO₂O | H | H | 6-F | H | H | |
| 338 | SO₂O | H | H | 4-Cl | H | H | |
| 339 | SO₂O | H | H | 5-Cl | H | H | |
| 340 | SO₂O | H | H | 4-CH₃ | H | H | |
| 341 | SO₂O | H | H | 5-CH₃ | H | H | |
| 342 | SO₂O | H | H | 4-CH₃ | H | H | |
| 343 | SO₂O | H | H | 5-CH₃ | H | H | |
| 344 | SO₂O | H | H | 4-Br | H | H | |
| 345 | SO₂O | H | H | 5-Br | H | H | |
| 346 | SO₂O | H | H | 4-CF₃ | H | H | |
| 347 | SO₂O | H | H | 5-CF₃ | H | H | |
| 348 | SO₂O | H | H | 4-NO₂ | H | H | |
| 349 | SO₂O | H | H | 5-NO₂ | H | H | |
| 350 | SO₂O | H | H | 4-CN | H | H | |
| 351 | SO₂O | H | H | 5-CN | H | H | |
| 352 | SO₂O | H | H | 4-F | 5-F | H | |

TABLE I-continued

| | | | | | | | | |
|---|---|---|---|---|---|---|---|---|
| 353 | SO$_2$O | H | H | 4-Cl | 5-Cl | H | | |
| 354 | SO$_2$O | H | H | 4-F | 5-Cl | H | | |
| 355 | SO$_2$O | H | H | 4-Cl | 5-F | H | | |
| 356 | SO$_2$O | H | H | 4-CH$_3$O | 5-Cl | H | | |
| 357 | SO$_2$O | H | H | 3-CH$_3$O | 5-F | H | | |
| 358 | SO$_2$O | H | H | H | H | 5-F | | |
| 359 | SO$_2$O | H | H | H | H | 6-Cl | | |
| 360 | CH(C$_6$H$_5$) | H | H | H | H | H | | |
| 361 | O | 3-Cl | H | 4-Cl | H | H | | |
| 362 | O | 3-CH$_3$O | 4-Cl | 5-F | H | H | | |
| 363 | CH$_2$O | 4-F | H | 5-CH$_3$O | H | H | | |
| 364 | SO$_2$O | 3-CH$_3$ | H | 4-F | H | H | | |
| 365+ | O | H | H | 4-CH$_3$CO | H | H | | |
| 366+ | O | H | H | 6-CH$_3$CO | H | H | | |
| 367* | O | H | H | 6-Br | H | H | | |
| 368 | O | H | H | 5-C$_6$H$_5$O | H | H | | |
| 369 | SO$_2$O | 3-NH$_2$ | H | H | H | H | | |
| 370 | COCH$_2$O | H | H | H | H | H | | |
| 371 | OCH$_2$ | 4-CH$_3$O | H | H | H | H | | |
| 372 | OCH$_2$ | 3-CH$_3$O | H | H | H | H | | |
| 373 | OCH$_2$ | 3-CN | H | H | H | H | | |
| 374 | OCH$_2$ | 4-CN | H | H | H | H | | |
| 375 | OCH$_2$ | 4-NO$_2$ | H | H | H | H | | |
| 376 | OCH$_2$ | 2-Cl | H | H | H | H | 7.58 | 120–122 |
| 377 | OCH$_2$ | 2-CH$_3$O | H | H | H | H | | |
| 378 | OCH$_2$ | 2-CN | H | H | H | H | | |
| 379 | (E)—N:N | 4-Cl | H | 4-CH$_3$O | H | H | 7.55 | Oil |
| 380 | CH(OH) | H | H | H | H | H | 7.58 | 142–143 |
| 381 | OCH$_2$ | 2-NO$_2$ | H | H | H | H | | |
| 382 | OCH$_2$ | 3-NO$_2$ | H | H | H | H | | |
| 383 | OCH$_2$ | 3-Br | H | H | H | H | | |
| 384 | OCH$_2$ | 3-Cl | H | H | H | H | | |
| 385 | OCH$_2$ | 3-C$_6$H$_5$O | H | H | H | H | | |
| 386 | OCH$_2$ | 4-Cl | H | H | H | H | | |
| 387 | S(O)CH$_2$ | 4-Cl | H | H | H | H | | |
| 388 | S(O)$_2$CH$_2$ | 4-Cl | H | H | H | H | | |
| 389 | OCH$_2$ | 2-Br | H | H | H | H | | |
| 390 | O | 2-NO$_2$ | 4-NO$_2$ | H | H | H | | |
| 391 | O | 2-Me | 3-Me | H | H | H | | |
| 392 | O | 2-Me | 4-Me | H | H | H | | |
| 393 | O | 2-Me | 5-Me | H | H | H | | |
| 394 | O | 2-Me | 6-Me | H | H | H | | |
| 395 | O | 3-Me | 4-Me | H | H | H | | |
| 396 | O | 3-Me | 5-Me | H | H | H | | |
| 397 | OCH$_2$ | 4-Br | H | H | H | H | | |
| 398 | CO$_2$CH$_2$ | H | H | H | H | H | | |
| 399 | SCH$_2$ | 2-Cl | H | H | H | H | | |
| 400 | SCH$_2$ | 4-NO$_2$ | H | H | H | H | | |
| 401 | S(O)CH$_2$ | 2-Cl | H | H | H | H | | |
| 402 | S(O)$_2$CH$_2$ | 2-Cl | H | H | H | H | | |
| 403 | (E/Z)—CH=CH | 4-NO$_2$ | H | H | H | H | | |
| 404 | Ph$_2$+PCH$_2$Br− | H | H | H | H | H | | |
| 405 | CH$_2$O | 4-t-C$_4$H$_9$ | H | H | H | H | | |
| 406 | CH$_2$OCO | H | H | H | H | H | | |
| 407 | CH$_2$NHCO | H | H | H | H | H | | |
| 408 | CH$_2$SCO | H | H | H | H | H | | |
| 409 | O$_2$C | 3-NO$_2$ | H | H | H | H | | |
| 410 | OCH$_2$O | 4-Cl | H | H | H | H | | |
| 411 | S(O)CH$_2$O | H | H | H | H | H | | |
| 412 | COCH(CH$_3$)O | H | H | H | H | H | | |
| 413 | (E)—CH$_2$ON:CH | H | H | H | H | H | | |
| 414 | (Z)—CH$_2$ON:CH | H | H | H | H | H | | |
| 415 | (CH$_2$)$_3$O | H | H | H | H | H | | |
| 416 | (CH$_2$)$_4$O | H | H | H | H | H | | |
| 417 | (CH$_2$)$_5$O | H | H | H | H | H | | |
| 418 | (E)—N:N | 4-OH | H | H | H | H | | |
| 419 | (E)—N:N | 4-CH$_3$O | H | H | H | H | | |
| 420 | CO.NH | 2-Br | H | H | H | H | | |
| 421 | CO.NH | 3-Br | H | H | H | H | | |
| 422 | CO.NH | 3-CH$_3$O | H | H | H | H | | |
| 423 | OCH$_2$CH$_2$O | H | H | H | H | H | | |
| 424 | SO$_2$O | | | | H | H | | |
| 425 | SCH$_2$O | H | | | H | H | | |
| 426 | CH$_2$O | 2-(CH$_3$O$_2$C—C=CH.OCH$_3$) | H | H | H | H | | |
| 427 | SO$_2$O | 4-CF$_3$O | H | H | H | H | | |
| 428 | SO$_2$O | 2-CH$_3$O$_2$C | H | H | H | H | | |
| 429 | CH$_2$CH$_2$CH(OH) | H | H | H | H | H | | |
| 430 | (E)—CH$_2$CH=CH | H | H | H | H | H | | |
| 431 | C(CH$_3$)(OH) | H | H | H | H | H | | |
| 432 | CH(OH) | 2-Cl | H | H | H | H | | |
| 433 | CH(OH) | 4-Cl | H | H | H | H | | |

TABLE I-continued

| | | | | | | | Olefinic+ | Melting Point (°C.) |
|---|---|---|---|---|---|---|---|---|
| 434 | CH(OH) | 2-CH₃O | H | H | H | H | | |
| 435 | CH(OH) | 3-CF₃ | H | H | H | H | | |
| 436 | CH(OH) | 3-CN | H | H | H | H | | |
| 437 | CH(OH) | 4-NO₂ | H | H | H | H | | |
| 438 | CH₂OSO₂ | H | H | H | H | H | | |
| 439 | CH₂NHCO.NH | H | H | H | H | H | | |
| 440 | CH₂NH | H | H | H | H | H | | |
| 441 | OCO.NH | H | H | H | H | H | | |
| 442 | NHCO.NH | H | H | H | H | H | | |
| 443 | CH₂OCO.NH | H | H | H | H | H | | |
| 444 | SO₂NH | 4-Br | H | H | H | H | | |
| 445 | CH₂NH | 3-CH₃ | H | H | H | H | | |
| 446 | O | H | H | H | H | H | 7.56 | 79-81 |
| 447 | O | 2-NH₂ | H | H | H | H | 7.57 | Oil |

TABLE I - FOOTNOTES:
+Chemical shift of singlet from olefinic proton on beta-methoxypropenoate group (p.p.m from tetramethylsilane).
Solvent: CDCl₃ unless otherwise stated.
Substituents D and G join to form a fused ring. Thus compound numbers 168, 169, 247, 248, 332 and 333 are:

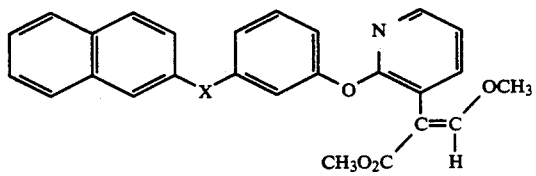

| X | COMPOUND |
|---|---|
| O | 168 |
| CH₂O | 247 |
| SO₂O | 332 |

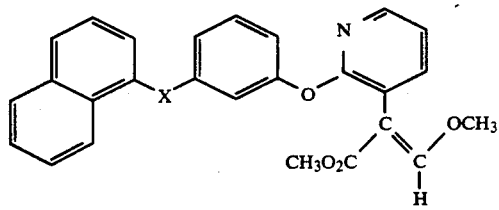

| X | COMPOUND |
|---|---|
| O | 169 |
| CH₂O | 248 |
| SO₂O | 333 |

And Compound No. 424 is:

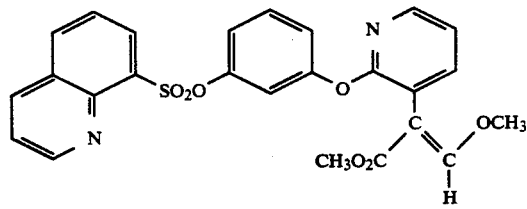

TABLE II

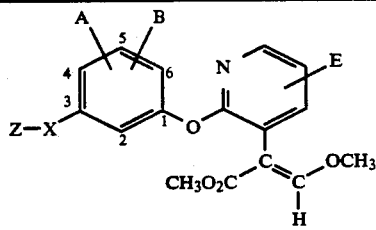

| Compound No. | Z | X | A | B | E | Olefinic+ | Melting Point (°C.) |
|---|---|---|---|---|---|---|---|
| 1 | Pyridin-2-yl | O | H | H | H | | |
| 2 | Pyridin-2-yl | S | H | H | H | | |
| 3 | Pyridin-2-yl | N(CH₃) | H | H | H | | |

TABLE II-continued

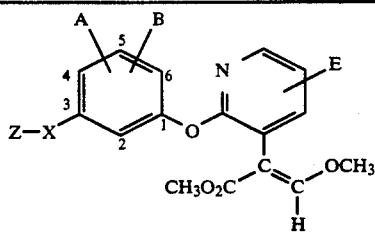

| Compound No. | Z | X | A | B | E | Olefinic+ | Melting Point (°C.) |
|---|---|---|---|---|---|---|---|
| 4 | Pyridin-2-yl | SO2O | H | H | H | | |
| 5 | Pyridin-2-yl | CH2CH2 | H | H | H | | |
| 6 | Pyridin-2-yl | OCH2 | H | H | H | 7.58 | Oil |
| 7 | Pyridin-2-yl | CH2O | H | H | H | | |
| 8 | Pyridin-3-yl | O | H | H | H | | |
| 9 | Pyridin-3-yl | S | H | H | H | | |
| 10 | Pyridin-3-yl | N(CH3) | H | H | H | | |
| 11 | Pyridin-3-yl | SO2O | H | H | H | | |
| 12 | Pyridin-3-yl | CH2CH2 | H | H | H | | |
| 13 | Pyridin-3-yl | OCH2 | H | H | H | | |
| 14 | Pyridin-3-yl | CH2O | H | H | H | | |
| 15 | Pyridin-4-yl | O | H | H | H | | |
| 16 | Pyridin-4-yl | S | H | H | H | | |
| 17 | Pyridin-4-yl | N(CH3) | H | H | H | | |
| 18 | Pyridin-4-yl | SO2O | H | H | H | | |
| 19 | Pyridin-4-yl | CH2CH2 | H | H | H | | |
| 20 | Pyridin-4-yl | OCH2 | H | H | H | | |
| 21 | Pyridin-4-yl | CH2O | H | H | H | | |
| 22 | Pyrimidin-2-yl | O | H | H | H | 7.57 | 151–153 |
| 23 | Pyrimidin-2-yl | S | H | H | H | | |
| 24 | Pyrimidin-4-yl | N(CH3) | H | H | H | | |
| 25 | Pyrimidin-4-yl | SO2O | H | H | H | | |
| 26 | Pyrimidin-5-yl | CH2CH2 | H | H | H | | |
| 27 | Pyrimidin-5-yl | CH2O | H | H | H | | |
| 28 | 1,2,4-Triazin-3-yl | OCH2 | H | H | H | | |
| 29 | 1,3,5-Triazin-2-yl | O | H | H | H | | |
| 30 | Pyrazin-2-yl | O | H | H | H | | |
| 31 | Pyrazin-2-yl | S | H | H | H | | |
| 32 | Pyrazin-2-yl | N(CH3) | H | H | H | | |
| 33 | Pyrazin-2-yl | SO2O | H | H | H | | |
| 34 | Pyrazin-2-yl | CH2O | H | H | H | | |
| 35 | Pyridazin-3-yl | O | H | H | H | | |
| 36 | Pyridazin-3-yl | S | H | H | H | | |
| 37 | Pyridazin-3-yl | SO2O | H | H | H | | |
| 38 | Quinolin-2-yl | O | H | H | H | | |
| 39 | Quinolin-2-yl | CH2O | H | H | H | | |
| 40 | Quinolin-3-yl | O | H | H | H | | |
| 41 | Quinolin-3-yl | SO2O | H | H | H | | |
| 42 | Benzoxazol-2-yl | O | H | H | H | | |
| 43 | Benzoxazol-2-yl | S | H | H | H | | |
| 44 | Benzoxazol-2-yl | N(CH3) | H | H | H | | |
| 45 | Benzoxazol-2-yl | SO2O | H | H | H | | |
| 46 | Benzthiazol-2-yl | CH2CH2 | H | H | H | | |
| 47 | Benzthiazol-2-yl | OCH2 | H | H | H | | |
| 48 | Benzthiazol-2-yl | CH2O | H | H | H | | |
| 49 | Thien-2-yl | CH2O | H | H | H | | |
| 50 | Thien-2-yl | CH2CH2 | H | H | H | | |
| 51 | Thien-3-yl | O | H | H | H | | |
| 52 | Thien-2-yl | SO2O | H | H | H | | |
| 53 | 5-CF3-Pyridin-2-yl | O | H | H | H | | |
| 54 | 5-CF3-Pyridin-2-yl | S | H | H | H | | |
| 55 | 5-CF3-Pyridin-2-yl | CH2O | H | H | H | | |
| 56 | 3-F-Pyridin-2-yl | O | H | H | H | | |
| 57 | 3-Cl-Pyridin-2-yl | O | H | H | H | | |
| 58 | 4-Br-Pyridin-2-yl | O | H | H | H | | |
| 59 | 5-CH3-Pyridin-2-yl | O | H | H | H | | |
| 60 | 6-CH3O-Pyridin-2-yl | O | H | H | H | | |
| 61 | 2-F-Pyridin-3-yl | O | H | H | H | | |
| 62 | 3-CF3-Pyridin-4-yl | O | H | H | H | | |
| 63 | 4,6-di-F-Pyridin-2-yl | O | H | H | H | | |
| 64 | 3-NO2-5-CF3-Pyridin-2-yl | O | H | H | H | | |
| 65 | 5-(CH3O2C)-Pyridin-2-yl | O | H | H | H | | |
| 66 | 3-CH3-Pyridin-2-yl | O | H | H | H | | |
| 67 | 4-CH3-Pyridin-2-yl | O | H | H | H | | |
| 68 | 6-CH3-Pyridin-2-yl | O | H | H | H | | |
| 69 | 5-(CN)-Pyridin-2-yl | O | H | H | H | | |

TABLE II-continued

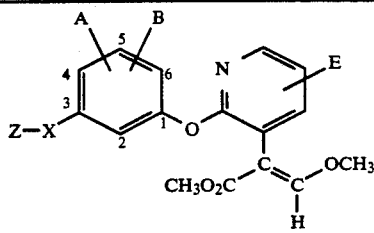

| Compound No. | Z | X | A | B | E | Olefinic+ | Melting Point (°C.) |
|---|---|---|---|---|---|---|---|
| 70 | 3-Cl-5-(C6H5O)-1,3,5-triazin-2-yl | O | H | H | H | | |
| 71 | Pyridin-2-yl | O | 2-F | H | H | | |
| 72 | Pyridin-2-yl | O | 4-Cl | H | H | | |
| 73 | Pyridin-4-yl | O | 5-CH3 | H | H | | |
| 74 | Pyridin-4-yl | O | 4-CH3O | H | H | | |
| 75 | 5-CF3-Pyridin-2-yl | O | 5-CN | H | H | | |
| 76 | 5-CF3-Pyridin-2-yl | O | 4-F | 5-CH3O | H | | |
| 77 | Pyrimidin-2-yl | O | H | H | 5-Cl | | |
| 78 | Pyrimidin-2-yl | O | H | H | 6-F | | |
| 79 | Benzoxazol-2-yl | O | 4-CF3O | H | 5-F | | |
| 80 | Benzoxazol-2-yl | O | 5-NO2 | H | H | | |
| 81 | 1,2,4-Triazol-1-yl | CH2 | H | H | H | | |
| 82 | 1,2,3-Triazol-1-yl | CH2 | H | H | H | | |
| 83 | Benzthiazol-2-yl | O | H | H | H | | |
| 84 | 3-Chloroquinoxalin-2-yl | O | H | H | H | | |
| 85 | Pyrimidin-2-yl | OCH2 | H | H | H | | |
| 86 | 3,5-di-Cl-1,3,5-triazin-2-yl | O | H | H | H | | |
| 87 | Pyrimidin-5-yl | O | H | H | H | | |
| 88 | 3-Cl,5-(CH3O)-1,3,5-triazin-2-yl | O | H | H | H | | |
| 89 | 6-Cl-Pyrimidin-4-yl | O | H | H | H | 7.59 | 82-84 |
| 90 | 5-Br-Pyrimidin-2-yl | O | H | H | H | | |
| 91 | 5-Cl-Pyrimidin-2-yl | O | H | H | H | | |
| 92 | Pyrimidin-4-yl | O | H | H | H | | |
| 93 | 2,6-Di-CH3O-Pyrimidin-4-yl | O | H | H | H | | |
| 94 | 2-Cl-6-CH3-Pyrimidin-4-yl | O | H | H | H | | |
| 95 | 2,6-Di-Cl-Pyrimidin-4-yl | O | H | H | H | | |
| 96 | 2,5,6-Tri-Cl-Pyrimidin-4-yl | O | H | H | H | | |
| 97 | 2-Cl-Pyrimidin-4-yl | O | H | H | H | 7.60 | 115-118 |
| 98 | 2-CH3-Thiazol-4-yl | CH2O | H | H | H | | |
| 99 | Benzoxazol-2-yl | OCH2 | H | H | H | | |
| 100 | Pyrazin-2-yl | OCH2 | H | H | H | | |
| 101 | 6-Cl-Pyrazin-2-yl | OCH2 | H | H | H | | |
| 102 | Quinolin-2-yl | OCH2 | H | H | H | | |
| 103 | 6-Cl-Pyridazin-3-yl | OCH2 | H | H | H | | |
| 104 | Pyridin-4-yl, N-oxide | OCH2 | H | H | H | | |
| 105 | 5-CF3-Pyridin-2-yl | OCH2 | H | H | H | | |
| 106 | 3-Cyanopyridin-2-yl | O | H | H | H | 7.58 | 109-112 |
| 107 | 5-NO2-Pyridin-2-yl | O | H | H | H | | |
| 108 | Pyrimidin-2-yl | CH2O | H | H | H | | |
| 109 | Pyrimidin-2-yl | SO2O | H | H | H | | |
| 110 | Pyrimidin-2-yl | NH | H | H | H | | |
| 111 | Pyrimidin-2-yl | N(CH3) | H | H | H | | |
| 112 | Pyrimidin-2-yl | CH2 | H | H | H | | |
| 113 | Pyrimidin-2-yl | CH(OH) | H | H | H | | |
| 114 | Pyrimidin-2-yl | CH2CH2 | H | H | H | | |
| 115 | Pyrimidin-4-yl | O | H | H | H | | |
| 116 | Pyrimidin-4-yl | CH2O | H | H | H | | |
| 117 | Pyrimidin-4-yl | OCH2 | H | H | H | | |
| 118 | Pyrimidin-4-yl | NH | H | H | H | | |
| 119 | Pyrimidin-4-yl | S | H | H | H | | |
| 120 | Pyrimidin-4-yl | CH2 | H | H | H | | |
| 121 | Pyrimidin-4-yl | CH(OH) | H | H | H | | |
| 122 | Pyrimidin-4-yl | CH2CH2 | H | H | H | | |
| 123 | Pyrimidin-5-yl | SO2O | H | H | H | | |
| 124 | Pyrimidin-5-yl | OCH2 | H | H | H | | |
| 125 | Pyrimidin-5-yl | NH | H | H | H | | |
| 126 | Pyrimidin-5-yl | N(CH3) | H | H | H | | |
| 127 | Pyrimidin-5-yl | S | H | H | H | | |
| 128 | Pyrimidin-5-yl | CH2 | H | H | H | | |
| 129 | Pyrimidin-5-yl | CH(OH) | H | H | H | | |
| 130 | 6-Chloropyridazin- | O | H | H | H | | |

TABLE II-continued

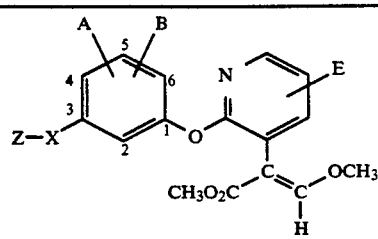

| Compound No. | Z | X | A | B | E | Olefinic+ | Melting Point (°C.) |
|---|---|---|---|---|---|---|---|
| 131 | 6-Chloropyridazin-3-yl | CH₂O | H | H | H | | |
| 132 | 6-Chloropyridazin-3-yl | NH | H | H | H | | |
| 133 | 6-Chloropyridazin-3-yl | N(CH₃) | H | H | H | | |
| 134 | 6-Chloropyridazin-3-yl | CH(OH) | H | H | H | | |
| 135 | Pyridazin-4-yl | O | H | H | H | | |
| 136 | Pyridazin-4-yl | OCH₂ | H | H | H | | |
| 137 | Pyridazin-4-yl | NH | H | H | H | | |
| 138 | Pyridazin-4-yl | SO₂O | H | H | H | | |
| 139 | 1,3,5-Triazin-2-yl | NH | H | H | H | | |
| 140 | 1,3,5-Triazin-2-yl | N(CH₃) | H | H | H | | |
| 141 | 1,2,4-Triazin-3-yl | O | H | H | H | | |
| 142 | 1,2,4-Triazin-3-yl | NH | H | H | H | | |
| 143 | 1,2,4-Triazin-3-yl | N(CH₃) | H | H | H | | |
| 144 | 1,2,4-Triazin-5-yl | O | H | H | H | | |
| 145 | 1,2,4-Triazin-5-yl | NH | H | H | H | | |
| 146 | 1,2,4-Triazin-6-yl | O | H | H | H | | |
| 147 | 1,2,4-Triazin-6-yl | N(CH₃) | H | H | H | | |
| 148 | Pyrimidin-2-yl, N-oxide | O | H | H | H | | |
| 149 | Pyrimidin-4-yl, 1-N-oxide | O | H | H | H | | |
| 150 | Pyrimidin-4-yl, 3-N-oxide | O | H | H | H | | |
| 151 | Pyridin-2-yl, N-oxide | O | H | H | H | | |
| 152 | Pyridin-3-yl, N-oxide | O | H | H | H | | |
| 153 | Pyrazin-2-yl, 1-N-oxide | O | H | H | H | | |
| 154 | Pyrazin-2-yl, 4-N-oxide | O | H | H | H | | |
| 155 | Pyridazin-3-yl, 1-N-oxide | O | H | H | H | | |
| 156 | Pyridazin-3-yl, 2-N-oxide | O | H | H | H | | |
| 157 | Isoquinolin-1-yl | O | H | H | H | | |
| 158 | Isoquinolin-1-yl | NH | H | H | H | | |
| 159 | Isoquinolin-1-yl | CH₂O | H | H | H | | |
| 160 | Isoquinolin-1-yl | OCH₂ | H | H | H | | |
| 161 | Isoquinolin-1-yl | CH(OH) | H | H | H | | |
| 162 | Isoquinolin-1-yl | S | H | H | H | | |
| 163 | Isoquinolin-1-yl | SO₂O | H | H | H | | |
| 164 | Quinolin-4-yl | O | H | H | H | | |
| 165 | Quinolin-4-yl | NH | H | H | H | | |
| 166 | Quinolin-4-yl | CH₂O | H | H | H | | |
| 167 | Quinolin-4-yl | OCH₂ | H | H | H | | |
| 168 | Quinolin-4-yl | CH(OH) | H | H | H | | |
| 169 | Quinolin-4-yl | S | H | H | H | | |
| 170 | Quinolin-4-yl | SO₂O | H | H | H | | |
| 171 | Quinazolin-4-yl | O | H | H | H | | |
| 172 | Quinazolin-4-yl | NH | H | H | H | | |
| 173 | Quinazolin-4-yl | CH₂O | H | H | H | | |
| 174 | Quinazolin-4-yl | OCH₂ | H | H | H | | |
| 175 | Quinazolin-4-yl | CH(OH) | H | H | H | | |
| 176 | Quinazolin-4-yl | S | H | H | H | | |
| 177 | Quinazolin-4-yl | SO₂O | H | H | H | | |
| 178 | 7-Chloroquinolin-4-yl | O | H | H | H | | |
| 179 | 7-Chloroquinolin-4-yl | S | H | H | H | | |
| 180 | 7-Chloroquinolin-4-yl | NH | H | H | H | | |
| 181 | Purin-6-yl | O | H | H | H | | |
| 182 | 2-Chloropurin-6-yl | S | H | H | H | | |
| 183 | 2-Chloropurin-6-yl | NH | H | H | H | | |
| 184 | 5-NO₂-Thien-2-yl | OCH₂ | H | H | H | | |
| 185 | 5-NO₂-Thien-2-yl | O | H | H | H | | |
| 186 | Thiazol-2-yl | CH₂O | H | H | H | | |
| 187 | Thiazol-2-yl | O | H | H | H | | |
| 188 | Thiazol-2-yl | NH | H | H | H | | |

TABLE II-continued

| Compound No. | Z | X | A | B | E | Olefinic+ | Melting Point (°C.) |
|---|---|---|---|---|---|---|---|
| 189 | Thiazol-4-yl | CH₂O | H | H | H | | |
| 190 | Thiazol-4-yl | O | H | H | H | | |
| 191 | Thiazol-4-yl | NH | H | H | H | | |
| 192 | Thiazol-5-yl | CH₂O | H | H | H | | |
| 193 | Thiazol-5-yl | O | H | H | H | | |
| 194 | Thiazol-5-yl | NH | H | H | H | | |
| 195 | Oxazol-2-yl | CH₂O | H | H | H | | |
| 196 | Oxazol-4-yl | O | H | H | H | | |
| 197 | Oxazol-5-yl | NH | H | H | H | | |
| 198 | 5-CF₃-1,3,4-Thiadiazol-2-yl | O | H | H | H | | |
| 199 | 5-CF₃-1,3,4-Thiadiazol-2-yl | OCH₂ | H | H | H | | |
| 200 | 4-Cl-1,2,5-Thiadiazol-3-yl | O | H | H | H | | |
| 201 | (thieno[3,2-d]pyrimidinyl) | O | H | H | H | | |
| 202 | (thieno[3,2-d]pyrimidinyl) | NH | H | H | H | | |
| 203 | (thieno[3,2-d]pyrimidinyl) | N(CH₃) | H | H | H | | |
| 204 | 4-Cl-Pyrimidin-2-yl | O | H | H | H | 7.58 | 92–96 |
| 205 | 4-Br-Pyrimidin-2-yl | O | H | H | H | | |
| 206 | 4-F-Pyrimidin-2-yl | O | H | H | H | | |
| 207 | 4-CH₃-Pyrimidin-2-yl | O | H | H | H | | |
| 208 | 4-CH₃O-Pyrimidin-2-yl | O | H | H | H | | |
| 209 | 4-CH₃CH₂O-Pyrimidin-2-yl | O | H | H | H | | |
| 210 | 4-NO₂-Pyrimidin-2-yl | O | H | H | H | | |
| 211 | 4-Cyano-Pyrimidin-2-yl | O | H | H | H | | |
| 212 | 4-CF₃-Pyrimidin-2-yl | O | H | H | H | | |
| 213 | 4-C₆H₅-Pyrimidin-2-yl | O | H | H | H | | |
| 214 | 4-C₆H₅O-Pyrimidin-2-yl | O | H | H | H | | |
| 215 | 5-F-Pyrimidin-2-yl | O | H | H | H | | |
| 216 | 5-CH₃-Pyrimidin-2-yl | O | H | H | H | | |
| 217 | 5-CH₃O-Pyrimidin-2-yl | O | H | H | H | | |
| 218 | 5-CH₃CH₂O-Pyrimidin-2-yl | O | H | H | H | | |
| 219 | 5-NO₂-Pyrimidin-2-yl | O | H | H | H | | |
| 220 | 5-Cyano-Pyrimidin-2-yl | O | H | H | H | | |
| 221 | 5-CF₃-Pyrimidin-2-yl | O | H | H | H | | |
| 222 | 5-C₆H₅-Pyrimidin-2-yl | O | H | H | H | | |
| 223 | 5-C₆H₅O-Pyrimidin-2-yl | O | H | H | H | | |
| 224 | 4,5-Di-Cl-Pyrimidin-2-yl | O | H | H | H | | |
| 225 | 4,6-Di-Cl-Pyrimidin-2-yl | O | H | H | H | | |
| 226 | 4-Cl-6-CH₃-Pyrimidin-2-yl | O | H | H | H | | |
| 227 | 4-Cl-5-CH₃O-Pyrimidin-2-yl | O | H | H | H | | |
| 228 | 2-F-Pyrimidin-4-yl | O | H | H | H | | |

TABLE II-continued

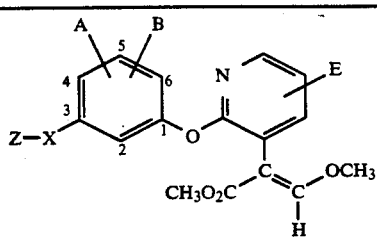

| Compound No. | Z | X | A | B | E | Olefinic+ | Melting Point (°C.) |
|---|---|---|---|---|---|---|---|
| 229 | 2-Br-Pyrimidin-4-yl | O | H | H | H | | |
| 230 | 2-CH$_3$-Pyrimidin-4-yl | O | H | H | H | | |
| 231 | 2-CH$_3$O-Pyrimidin-4-yl | O | H | H | H | | |
| 232 | 2-CH$_3$CH$_2$O-Pyrimidin-4-yl | O | H | H | H | | |
| 233 | 2-NO$_2$-Pyrimidin-4-yl | O | H | H | H | | |
| 234 | 2-CH$_3$S-Pyrimidin-4-yl | O | H | H | H | | |
| 235 | 2-Cyano-Pyrimidin-4-yl | O | H | H | H | | |
| 236 | 2-CF$_3$-Pyrimidin-4-yl | O | H | H | H | | |
| 237 | 2-C$_6$H$_5$O-Pyrimidin-4-yl | O | H | H | H | | |
| 238 | 2-C$_6$H$_5$-Pyrimidin-4-yl | O | H | H | H | | |
| 239 | 6-F-Pyrimidin-4-yl | O | H | H | H | | |
| 240 | 6-Br-Pyrimidin-4-yl | O | H | H | H | | |
| 241 | 6-CH$_3$-Pyrimidin-4-yl | O | H | H | H | | |
| 242 | 6-CH$_3$O-Pyrimidin-4-yl | O | H | H | H | | |
| 243 | 6-CH$_3$CH$_2$O-Pyrimidin-4-yl | O | H | H | H | | |
| 244 | 6-NO$_2$-Pyrimidin-4-yl | O | H | H | H | | |
| 245 | 6-Cyano-Pyrimidin-4-yl | O | H | H | H | | |
| 246 | 6-CF$_3$-Pyrimidin-4-yl | O | H | H | H | | |
| 247 | 6-C$_6$H$_5$O-Pyrimidin-4-yl | O | H | H | H | | |
| 248 | 6-C$_6$H$_5$-Pyrimidin-4-yl | O | H | H | H | | |
| 249 | 5-F-Pyrimidin-4-yl | O | H | H | H | | |
| 250 | 5-Cl-Pyrimidin-4-yl | O | H | H | H | | |
| 251 | 5-Br-Pyrimidin-4-yl | O | H | H | H | | |
| 252 | 5-CH$_3$-Pyrimidin-4-yl | O | H | H | H | | |
| 253 | 5-CH$_3$O-Pyrimidin-4-yl | O | H | H | H | | |
| 254 | 5-CH$_3$CH$_2$O-Pyrimidin-4-yl | O | H | H | H | | |
| 255 | 5-NO$_2$-Pyrimidin-4-yl | O | H | H | H | | |
| 256 | 5-Cyano-Pyrimidin-4-yl | O | H | H | H | | |
| 257 | 5-CF$_3$-Pyrimidin-4-yl | O | H | H | H | | |
| 258 | 5-C$_6$H$_5$O-Pyrimidin-4-yl | O | H | H | H | | |
| 259 | 5-C$_6$H$_5$-Pyrimidin-4-yl | O | H | H | H | | |
| 260 | 2-Cl-Pyrimidin-5-yl | O | H | H | H | | |
| 261 | 2-CH$_3$-Pyrimidin-5-yl | O | H | H | H | | |
| 262 | 2-F-Pyrimidin-5-yl | O | H | H | H | | |
| 263 | 2-CH$_3$O-Pyrimidin-5-yl | O | H | H | H | | |
| 264 | 2-Cyano-Pyrimidin-5-yl | O | H | H | H | | |
| 265 | 4-CH$_3$-Pyrimidin-5-yl | O | H | H | H | | |
| 266 | 4-CH$_3$O-Pyrimidin-5-yl | O | H | H | H | | |
| 267 | 4-CF$_3$-Pyrimidin-5-yl | O | H | H | H | | |
| 268 | 2,4-di-CH$_3$-Pyrimidin-5-yl | O | H | H | H | | |
| 269 | 2-CH$_3$S-4-CH$_3$O-Pyrimidin-5-yl | O | H | H | H | | |
| 270 | Pyrrol-2-yl | CONH | H | H | H | | |
| 271 | 6-Cl-3-NO$_2$-Pyridin-2-yl and 6-Cl-5-NO$_2$-Pyridin-2-yl, 1:1 mixture | O | H | H | H | | |
| 272 | 3,6-Di-CH$_3$-Pyrazin-2-yl | O | H | H | H | | |
| 273 | 6-Cl-Pyrazin-2-yl | O | H | H | H | | |
| 274 | 6-CH$_3$O-Pyridazin-3-yl | O | H | H | H | | |
| 275 | 6-Cl-4-CH$_3$-Pyridazin-3-yl | O | H | H | H | | |
| 276 | 6-Cl-5-CH$_3$-Pyridazin-3-yl | O | H | H | H | | |
| 277 | 4-CF$_3$-Pyridin-2-yl | O | H | H | H | | |
| 278 | 6-Cyanopyridin-2-yl | O | H | H | H | | |
| 279 | 4-Cyanopyridin-2-yl | O | H | H | H | | |
| 280 | 4-Acetylpyridin-2-yl | O | H | H | H | | |
| 281 | 6-C$_6$H$_5$-Pyridazin-3-yl | O | H | H | H | | |
| 282 | 3-(CH$_3$O$_2$C)-Pyridin-2-yl | O | H | H | H | | |
| 283 | 5-(CH$_3$O$_2$C)-Pyridin-3-yl | O | H | H | H | | |

TABLE II-continued

[Structure: phenyl ring with positions 1-6, substituents A (5), B (5), Z-X at position 3, linked via O to pyridine with E substituent, bearing C(CO2CH3)=C(OCH3)H group]

| Compound No. | Z | X | A | B | E | Olefinic+ | Melting Point (°C.) |
|---|---|---|---|---|---|---|---|
| 284 | 4-CF$_2$Cl-Pyridin-2-yl | O | H | H | H | | |
| 285 | 3,5-Di-CF$_3$-Pyridin-2-yl | O | H | H | H | | |
| 286 | 6-CF$_3$-Pyridin-2-yl | O | H | H | H | | |
| 287 | 5-CF$_3$-Pyridin-3-yl | O | H | H | H | | |
| 288 | 2-Cl-Pyridin-3-yl | O | H | H | H | | |
| 289 | 2-CH$_3$O-Pyridin-3-yl | O | H | H | H | | |
| 290 | 2-Cl-Pyridin-4-yl | O | H | H | H | | |
| 291 | 2-CH$_3$O-Pyridin-4-yl | O | H | H | H | | |
| 292 | 2-Cl-Pyridin-5-yl | O | H | H | H | | |
| 293 | 2-CH$_3$O-Pyridin-5-yl | O | H | H | H | | |
| 294 | 3-CH$_3$S-Pyridin-2-yl | O | H | H | H | | |
| 295 | 4-CF$_3$O-Pyridin-2-yl | O | H | H | H | | |
| 296 | 4-CON(CH$_3$)$_2$-Pyridin-2-yl | O | H | H | H | | |
| 297 | 3-Cl-1,2,4-Oxadiazol-5-yl | O | H | H | H | | |
| 298 | 3-Cl-1,2,4-Oxadiazol-5-yl | S | H | H | H | | |
| 299 | 5-CH$_3$S-1,2,4-Oxadiazol-3-yl | O | H | H | H | | |
| 300 | Pyridin-2-yl | CH(OH) | H | H | H | | |
| 301 | Pyridin-3-yl | CH(OH) | H | H | H | | |
| 302 | Pyridin-4-yl | CH(OH) | H | H | H | | |
| 303 | Pyridin-2-yl | CO | H | H | H | | |
| 304 | Pyridin-3-yl | CO | H | H | H | | |
| 305 | Pyridin-4-yl | CO | H | H | H | | |
| 306 | Thien-2-yl | CH(OH) | H | H | H | | |
| 307 | Furan-2-yl | CH(OH) | H | H | H | | |
| 308 | N-CH$_3$-Pyrrol-2-yl | CH(OH) | H | H | H | | |
| 309 | N-CH$_3$-Pyrrol-2-yl | CO | H | H | H | | |
| 310 | 6-Br-Pyridin-2-yl | OCH$_2$ | H | H | H | | |
| 311 | 2-Cl-Pyrimidin-4-yl | OCH$_2$ | H | H | H | | |
| 312 | 2,6-Di-F-Pyrimidin-4-yl | O | H | H | H | | |
| 313 | 2-CH$_3$S-6-CH$_3$-Pyrimidin-4-yl | O | H | H | H | | |
| 314 | 2-CH$_3$S-Pyrimidin-4-yl | O | H | H | H | | |
| 315 | N-CH$_3$-Pyrrol-2-yl | CON(CH$_3$) | H | H | H | | |
| 316 | 5-CF$_3$-Pyridin-2-yl | NH | H | H | H | | |
| 317 | 2-Cl-Pyrimidin-4-yl | NH | H | H | H | | |
| 318 | 4-Cl-Pyrimidin-2-yl | NH | H | H | H | | |
| 319 | 5-NO$_2$-6-(CH$_3$)$_2$N-Pyridin-2-yl | O | H | H | H | | |
| 320 | 3-NO$_2$-Pyridin-2-yl | O | H | H | H | 7.59 | 128–130 |
| 321 | 5-NO$_2$-Thiazol-2-yl | O | H | H | H | 7.60 | Gum |
| 322 | 2-CH$_3$SO$_2$-Pyrimidin-4-yl | O | H | H | H | 7.59 | Foam |

FOOTNOTES:
+Chemical shift of singlet from olefinic proton on beta-methoxypropenoate group (p.p.m from tetramethylsilane).
Solvent: CDCl$_3$ unless otherwise stated.

TABLE III

[Structure: D,G-substituted phenyl linked via X to A,B-substituted phenyl, linked via S to pyridine with E, bearing C(CO2CH3)=C(OCH3)H group]

Table III comprises 447 compounds of the general structure above with all the values of D, G, X, A, B and E listed in Table I. That is, Compound Nos. 1 to 447 of Table III are the same as those of Table I except that the value of K is oxygen in Table I and sulphur in Table III.

TABLE IV

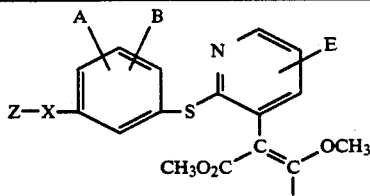

Table IV comprises 322 compounds of the general structure above with all the values of Z, X, A, B and E listed in Table II. That is, compounds Nos. 1 to 322 of Table IV are the same as those of Table II except that the value of K is oxygen in Table II and sulphur is Table IV.

TABLE V: SELECTED PROTON NMR DATA

Table V shows selected proton n.m.r data for certain compounds described in Tables I, II, III and IV. Chemical shifts are measured in p.p.m from tetramethylsilane, and deuterochloroform was used as solvent throughout. The column headed 'frequency' refers to the operating frequency of the n.m.r spectrometer. The following abbreviations are used:

br=broad
s=singlet
d=doublet
t=triplet
q=quarter
m=multiplet

| TABLE NO. | COMPOUND NO. | FREQUENCY (MHz) | ppm. |
|---|---|---|---|
| I | 21 | 270 | 3.68(3H, s); 3.85 (3H, s); 5.08(2H, s); 6.90–7.40(m); 7.58 (1H, s); 7.63(1H, m); 8.12(1H, m)ppm. |
| I | 128 | 270 | 3.67(3H, s); 3.82(6H, s); 6.68–7.28(9H, m); 7.57(1H, s); 7.61(1H, d); 8.23(1H, d)ppm. |
| I | 134 | 270 | 3.69(3H, s); 3.85(3H, s); 6.83–7.17(6H, m); 7.34–7.52(2H, m); 7.58 (1H, s); 7.64(2H, m); 8.14(1H, m)ppm. |
| I | 447 | 270 | 3.66(3H, s); 3.78(2H, br s); 3.84(3H, s); 6.67–7.30(9H, m); 7.57 (1H, s); 7.60(1H, m); 8.19(1H, m)ppm. |
| II | 6 | 270 | 3.68(3H, s); 3.85(3H, s); 5.38(2H, s); 6.75–6.87(1H, m); 6.98–7.06 (1H, m); 7.17–7.25(4H, m); 7.32–7.40(1H, m); 7.58(1H, s); 7.55–7.64 (2H, m); 8.09–8.17(2H, m) ppm. |
| II | 321 | 270 | 3.70(3H, s); 3.86(3H, s); 7.05–7.15(4H, m); 7.44–7.50(1H, t); 7.60 (1H, s); 7.64–7.68(1H, m); 8.12–8.15(2H, m) ppm. |
| II | 322 | 270 | 3.21(3H, s); 3.70(3H, s); 3.84(3H, s); 6.90–7.10(5H, m); 7.39–7.47 (1H, 5); 7.56–7.70(1H, m); 7.59(1H, s); 8.12 (1H, m); 8.74(1H, d) |

-continued

| TABLE NO. | COMPOUND NO. | FREQUENCY (MHz) |
|---|---|---|
| | | ppm. |

The compounds of the invention of formula (I) can be made by a variety of methods, and some of these are illustrated in Schemes I to VI. Throughout these Schemes, the terms K, Z, X, A, B, E, $R^1$, $R^2$, $R^3$, $R^4$ and $R^5$ are as defined above, $R^6$ is hydrogen or a metal (such as sodium or potassium), R is an alkyl group, and L is a leaving group such as a halide (chloride, bromide or iodide), a $CH_3SO_4$-anion, or a sulphonyloxyanion. Each of the transformations described in Schemes I to VI is performed at a suitable temperature and either in a suitable solvent or in the absence of a solvent.

Scheme I illustrates ways in which the methyl beta-methoxypropenoate group can be constructed in the final stages of the preparation of the compounds of the invention from precursors with a preformed framework of 3 aromatic rings. Alternatively, the methyl beta-methoxy-propenoate group may be constructed at an earlier stage of the preparation, in which case the final step or steps comprise elaboration of other parts of the compounds of the invention to form the framework of 3 aromatic rings. Examples of procedures of this kind are shown in Schemes II to VI.

In whichever order the steps are carried out to prepare the compounds of the invention, the ether linkage which is common to all the compounds of the invention can be prepared by one of the coupling reactions shown in Scheme II. For a review of the Ullman ether synthesis see A. A. Moroz and M. S. Shrartsberg, *Russian Chem. Reviews*, 1974, 43, 679. These couplings are often performed in the presence of a catalyst which consists of a transition metal or a salt or compound of a transition metal, such as copper or a copper salt or compound, or a mixture thereof. In Scheme II, the term W represents either the group Z—X—, wherein Z and X are as defined above, or a group which can be converted by standard procedures described in the chemical literature into the group Z—X—. For example, W can be OH, SH, or —$NHR^4$. The term Y represents either the alpha-linked methyl beta-methoxypropenoate group of the compounds of the invention or a group which can be converted into such a group by standard methods described in the chemical literature and/or described in Scheme I and the following paragraphs. For example, Y can be —$CH_2CO_2H$, —$CH_2CO_2Me$ or —CHO. In the context of Scheme II, the term L is preferably a halogen. Thus compounds of formula (XI) react with compounds of formula (XII) under the conditions of the Ullmann reaction already described to give the intermediates of formula (VIII). As an example of one of the coupling reactions shown in Scheme II, substituted 3-phenoxyphenols, as their salts, undergo coupling with 2-bromo- or 2-chloro-3-cyanopyridine to give, substituted 2-(3-phenoxyphenoxy)-3-cyanopyridines.

In one particular aspect, the invention includes a process for the preparation of the compound of formula (I) which comprises reacting a compound of general formula (XIIa):

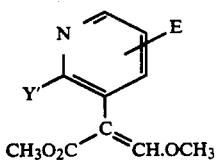

(XIIa)

wherein Y' is halogen or other good leaving group (e.g. $C_{1-4}$ alkylsulphonyl, optionally substituted aryl(suitably phenyl)sulphonyl and nitro), with a phenol or thiophenol of general formula (XIa):

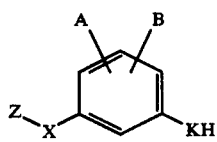

(XIa)

in the presence of a base, or with a salt of the phenol or thiophenol (XIa), preferably in the presence of a catalyst which comprises a suitable transition metal, a transition metal salt or compound or a mixture thereof.

The compounds of the invention of formula (I) can be prepared from the pyridylacetates of formula (III) or the ketoesters of formula (VI) by the steps shown in Scheme I.

Thus compounds of formula (I) can be prepared by treatment of pyridylacetates of formula (III) with a base (such as sodium hydride or sodium methoxide) and methyl formate. If a species of formula $CH_3L$, wherein L is as defined above, is then added to the reaction mixture, compounds of formula (I) may be obtained. If a protic acid is added to the reaction mixture, compounds of formula (II) wherein $R^5$ is hydrogen are obtained. Alternatively, the species of formula (II) wherein $R^5$ is a metal (such as sodium) may themselves be isolated from the reaction mixture.

Compounds of formula (II) wherein $R^5$ is a metal can be converted into compounds of formula (I) by treatment with a species of formula $CH_3L$, wherein L is as defined above. Compounds of formula (II) wherein $R^5$ is hydrogen can be converted into compounds of formula (I) by successive treatments with a base (such as potassium carbonate) and a species of general formula $CH_3L$.

Alternatively, compounds of formula (I) can be prepared from acetals of formula (IV) by elimination of methanol under either acidic or basic conditions. Examples of reagents or reagent mixtures which can be used for this transformation are lithium di-isopropylamide; potassium hydrogen sulphate (see, for example T Yamada, H Hagiwara and H Uda, *J. Chem. Soc., Chemical Communications*, 1980, 838, and references therein); and triethylamine, often in the presence of a Lewis acid such as titanium tetrachloride (see, for example, K Nsunda and L Heresi, *J. Chem. Soc., Chemical Communications*, 1985, 1000).

Acetals of formula (IV) can be prepared by treatment of methyl silyl ketene acetals of formula (V) wherein R is an alkyl group, with trimethyl orthoformate in the presence of a Lewis acid such as titanium tetrachloride (see, for example, K Saigo, M Osaki and T Mukaiyama, *Chemistry Letters*, 1976, 769).

Methyl silyl ketene acetals of formula (V) can be prepared from pyridylacetates of formula (III) by treatment with a base and a trialkylsilyl halide of formula $R_3SiCl$ or $R_3SiBr$, such as trimethylsilyl chloride, or a base (such as triethylamine) and a trialkylsilyl triflate of formula $R_3Si$—$OSO_2CF_3$ (see, for example, C Ainsworth, F Chen and Y Kuo, *J. Organometallic Chemistry*, 1972, 46, 59).

It is not always necessary to isolate the intermediates (IV) and (V); under appropriate conditions, compounds of formula (I) may be prepared from pyridylacetates of formula (III) in "one pot" by the successive addition of suitable reagents listed above.

Alternatively, compounds of formula (I) can be prepared by treatment of ketoesters of formula (VI) with, for example, methoxymethylenetriphenylphosphorane (see, for example, W Steglich, G Schramm, T Anke and F Oberwinkler, EP 0044448, 4.7.1980).

Ketoesters of formula (VI) may be prepared by methods described in the literature. Particularly useful methods include (i) the reaction of appropriate pyridylmagnesium halides or pyridyl-lithium species with dimethyl oxalate using the method described by L M Weinstock R B Currie and A V Lovell, *Synth. Commun.*, 1981, 11, 943 and references therein; (ii) oxidation of pyridylacetates of formula (III) using selenium dioxide, generally in the absence of a solvent, and generally at a temperature above 100° C.; and (iii) oxidation of (3-pyridyl)-glycolic acid esters using, for example, manganese oxide in a suitable solvent.

Pyridylacetates of formula (III) and the corresponding pyridylacetic acids of formula (VII) may also be prepared by numerous other methods described int he chemical literature. For example, several useful methods are described by D C Atkinson, K E Godfrey, B Meek, J F Saville and M R Stillings, *J. Med. Chem.*, 1983, 26, 1353 and D C Atkinson, K E Godfrey, P L Meters, N C Phillips, M R Stillings and A P Welbourn, *J. Med. Chem.*, 1983, 26, 1361. Furthermore, many of the methods described for the preparation of 2-arylpropionic esters and acids by J-P Rieu, A Boucherle, H Cousse and G Mouzin, *Tetrahedron*, 1986, 42, 4095, are also applicable to the preparation of pyridylacetates of formula (III) and pyridylacetic acids of formula (VII) using appropriate precursors wherein the ortho-substituted phenoxy substituent and the substituent E are already present.

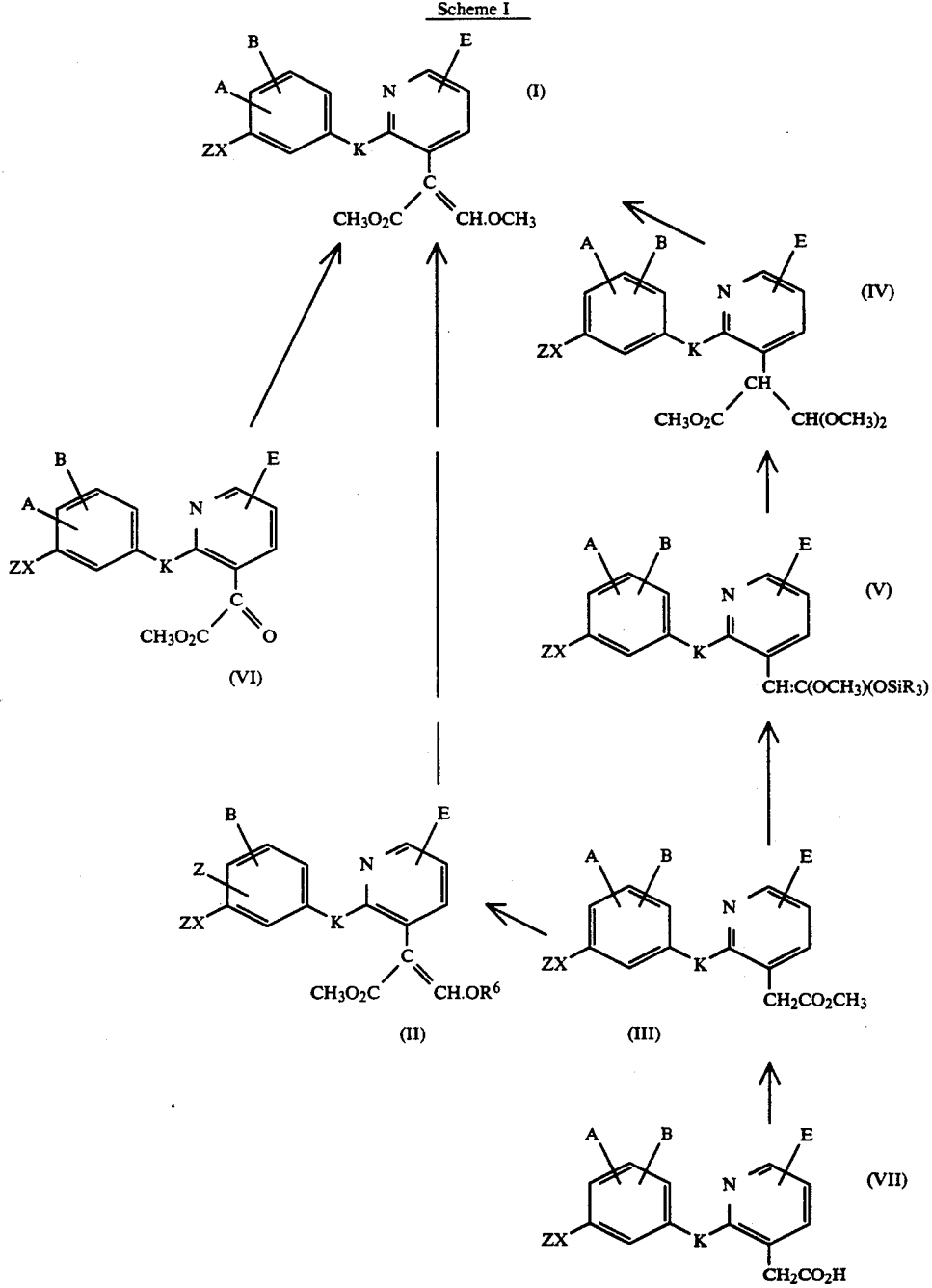
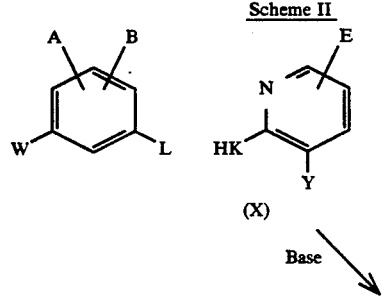
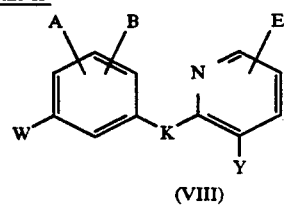

-continued
Scheme II

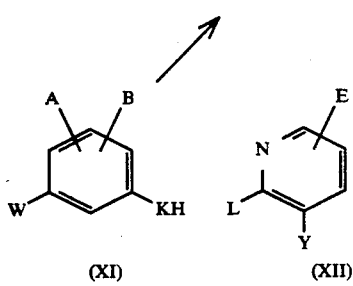

(XI)     (XII)

Schemes III, IV, V, VI and VII illustrate examples of intermediates containing the methyl beta-methoxypropenoate group and show how they may be converted into certain specific types of compound of the invention (I).

Thus, in Scheme III, in the presence of a base, and sometimes in the presence of a transition metal or transition metal salt catalyst, such as a copper to copper salt catalyst, compounds of formula (XIII) react with aromatic or heteroaromatic compounds of formula ZL, wherein Z and L are as defined above, or with iodonium salts of formula $Z_2I^+T^-$, wherein Z is as defined as above and T is a counter ion, such as a halide ion, or with aryl or heteroarylbismuth species, to give compounds of formula (XIV). In addition, in the presence of a base, compounds of formula (XIII) react with aryl- or heteroarylsulphonyl halides of formula $ZSO_2Q$, wherein Z is as defined above and Q is a halogen, to give compounds of formula (XV). Furthermore, and also in the presence of a base, compounds of formula (XIII) react with arylalkyl or heteroarylalkyl species of formula $ZCHR^1L$, wherein Z, $R^1$ and L are as defined above, to give compounds of formula (XVI).

In Scheme IV the thiols of formula (XVII), generally in the presence of a base, react with aromatic or heteroaromatic compounds of formula ZL, or with iodonium salts of formula $Z_2I^+T^-$, or with aryl- or heteroarylbismuth species, to give compounds of formula (XVIII) in ways which are analogous to the reactions of the corresponding phenols of formula (XIII). Similarly, and again in the presence of a base, the thiols of formula (XVII) react with arylalkyl or heteroarylalkyl species of formula $ZCHR^1L$ to give compounds of formula (XIX). The sulphides of formula (XVIII) and (XIX) can be oxidised to the corresponding sulphoxides and sulphones by standard methods described in the chemical literature.

In Scheme V, compounds of formula (XX) react with hydroxy-derivatives of aromatic or heteroaromatic compounds of formula ZOH, wherein Z is as defined above, often in the presence of a base, to form compounds of formula (XXI). Further more, compounds of formula (XX) react with trialkylphosphites of formula $P(OR)_3$ or with species of formula $M^+P^-(O)(OR)_2$, wherein R is as defined above in each case and M is a metal such as sodium or lithium, to give phosphonates of formula (XXII). Phosphonates of formula (XXII), in the presence of a base, react with aldehydes or ketones of formula $ZR^1C:O$, wherein Z and $R^1$ are as defined above, to give olefins of formula (XXIV). In addition, aldehydes or ketones of formula (XXIII), on treatment with phosphonate anions of formula $ZR^1C^- P(O)(OR)_2M^+$, wherein Z, R, $R^1$ and M are as defined above, or with the corresponding phosphoranes, also give olefins of formula (XXIV). The olefins of formula (XXIV) can be reduced to the compounds of formula (XXV) by, for example, hydrogenation over an appropriate catalyst.

In Scheme VI, compounds of formula (XXVI), in the presence of a base, react with acid halides of formula ZCOQ, wherein Z and Q are as defined above, or, in the presence of an appropriate dehydrating agent, react with acids of formula $ZCO_2H$, wherein Z is as defined above, to give compounds of formula (XXVII).

Intermediates of formula (XXVI) can also be converted into other types of compound of the invention of formula (I) by methods described in the chemical literature. For example, compounds of formula (XXVI) wherein $R^4$ is hydrogen can be converted, via diazotisation, into the corresponding sulphonyl chlorides (compare *Organic Syntheses*, 1981, 60, 121) and then, by treatment with alcohols or phenols in the presence of a base into sulphonic esters.

Compounds of the invention of formula (I) wherein at least one of A and B are hydrogen may be converted into compounds of the invention of formula (I) wherein at least one of A and B are certain substituents (such as a halogen or a nitro or acyl group) by electrophilic substitution processes of the kind described in the chemical literature.

The intermediates of formulae (XIII), (XVII), (XX), (XXIII) and (XXVI) can be prepared by processes described in the chemical literature and by processes of the kinds described in Schemes I and II. For example, compounds of formula (XX) where L is bromine can be made from compounds of formula (XX) where L is H, by reaction with N-bromosuccinimide or N,N-dibromodimethylhydantoin, in the presence or absence of irradiation by light.

The intermediates of formulae (IX), (X), (XI), (XII), ZL, $Z_2I^+T^-$, $ZCHR^1L$, $ZSO_2Q$, ZOH, $ZR^1C:O$, $ZR^1C^- P(O)(OR)_2M^+$, ZCOQ and $ZCO_2H$ can be made by methods described in the chemical literature.

Scheme III

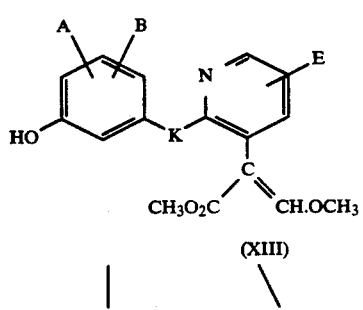

(XIII)

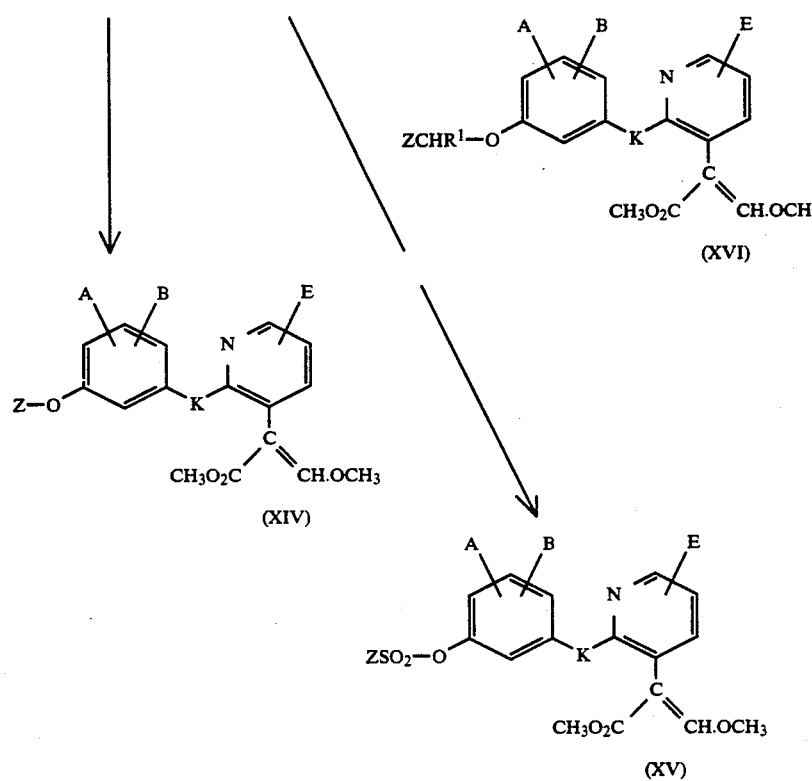
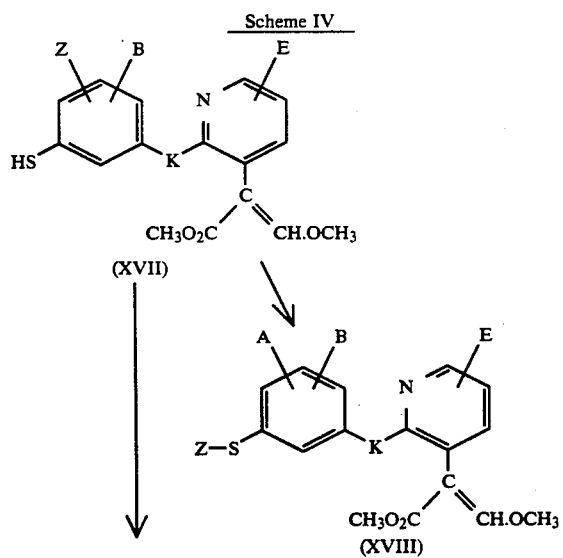
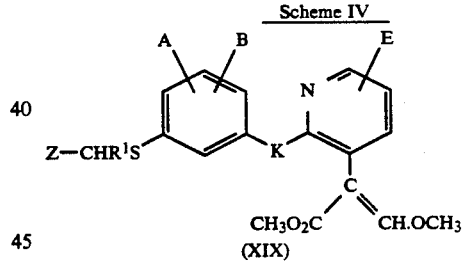
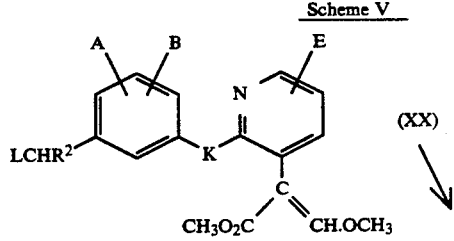

Scheme V

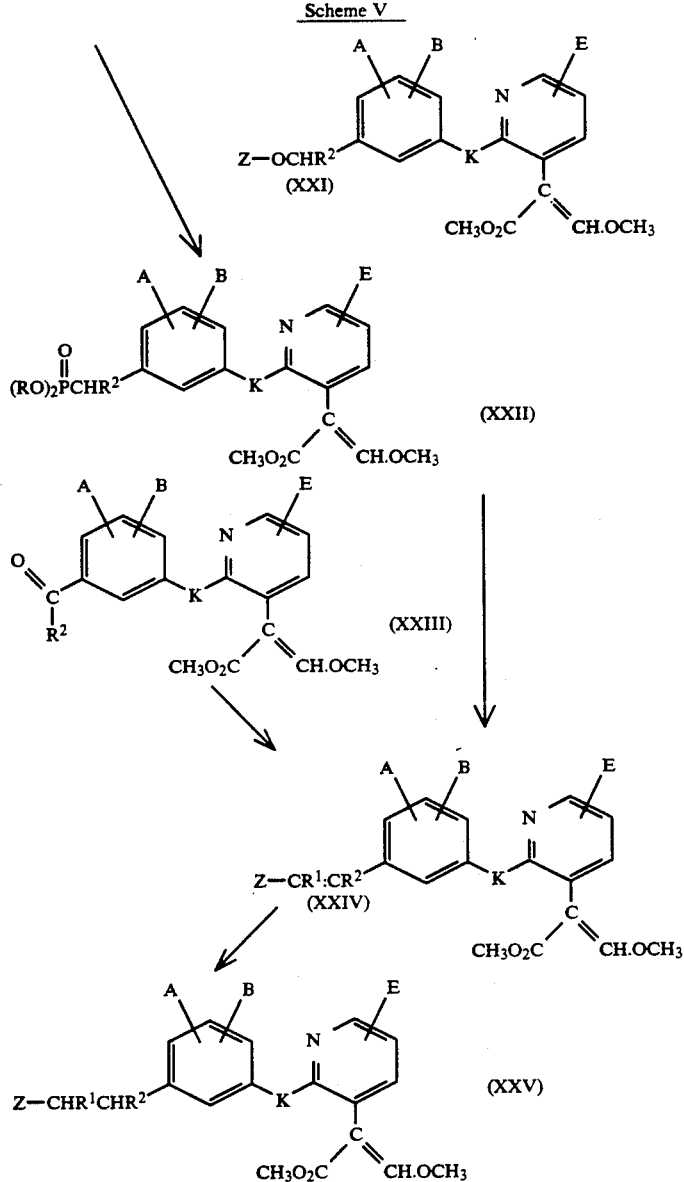

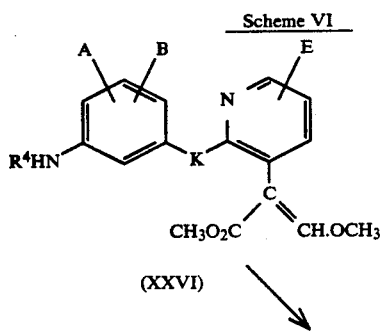

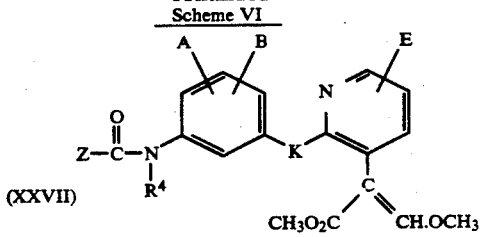

In Scheme VII compounds of formula (XXVIII) can be oxidised, for example using pyridinium dichromate in a suitable solvent (such as methylene chloride) or oxalyl chloride in dimethyl sulphoxide in the presence of a base (the Swern oxidation), to give aldehydes (where $R^2$ is H) or ketones (where $R^2$ is alkyl) of formula (XXIII). The aldehydes or ketones of formula (XXIII) can react with oxyamines of formula $ZONH_2$ or $ZCHR^1ONH_2$, or with hydrazines of formula ZNR$^1$NH$_2$, wherein Z and R$^1$ are as defined above, to give compounds of the invention of formula (I) where X is the group ON=CR$^2$, CHR$^1$ON=CR$^2$, or NR$^1$N=CR$^2$ respectively. Also, compounds of formula (XXIII) can react with Grignard reagents of formula ZMgHal or ZCR$^1$R$^2$MgHal, where Hal is chlorine, bromine or iodine and Z, R$^1$ and R$^2$ are as defined above, to give compounds of the invention of formula (I) where X is CR$^2$(OH) or CR$^1$R$^2$CR$^2$(OH) respectively. Also, compounds of formula (XXIII) can react with amines of formula ZNHR$^1$ or ZCR$^1$R$^2$NHR$^1$, wherein Z, R$^1$ and R$^2$ are as defined above, in the presence of a reducing agent (such as sodium cyanoborohydride or hydrogen gas in the presence of a suitable metal catalyst) to give compounds of the invention of formula (I) where X is NR$^1$CHR$^2$ or CR$^1$R$^2$NR$^1$CHR$^2$. When the reducing agent is left out and when R$^1$ is H, then the immediately preceding procedure will give compounds of the invention of formula (I) where X is N=CR$^2$ or CR$^1$R$^2$N=CR$^2$.

Compounds of formula (XXVIII) where R$^2$ is H, can also be oxidised to carboxylic acids of formula (XXIX), using for example Jones' reagent (chromium trioxide in sulphuric acid). The carboxylic acids (XXIX) can be converted directly into compounds of the invention of formula (I) where, for example, X is O$_2$C, CHR$^1$OCO, SCO, CHR$^1$SCO, NR$^4$CO or CHR$^1$NR$^4$CO, using one of the standard coupling reagents well known in the literature, such as dicyclohexylcarbodiimide or carbonyldiimidazole, in a suitable solvent.

Alternatively, the carboxylic acids of formula (XXIX) can be converted into the acid chlorides of formula (XXX) by treatment with, for example, thionyl chloride or oxalyl chloride. The acid chlorides of formula (XXX) can then react, for example, with compounds of formula ZOH, ZCHR$^1$OH, ZSH, ZCHR$^1$SH, ZNR$^4$H or ZCHR$^1$NR$^4$H in a suitable solvent, in the presence of a base, to give compounds of the invention of formula (I) where X is O$_2$C, CHR$^1$OCO, SCO, CHR$^1$SCO, NR$^4$CO, or CHR$^1$NR$^4$CO respectively.

Compounds of formula (XXVIII) can also react directly with compounds of formula ZL, optionally in the presence of a base, where Z is a reactive aromatic group (for example nitrophenyl) or heteroaromatic group (for example 2-pyridyl or 2-pyrimidinyl) to give compounds of the invention of formula (XXI). It may be necessary first to generate the oxygen anion of compounds of formula (XXVIII) with a strong base such as sodium hydride.

Additionally, compounds of formula (XXVIII) can be converted into compounds of formula (XX) by treatment, for example, with a halogenation agent such as thionyl chloride or phosphorus tribromide, where L is chlorine or bromine, or by treatment with a sulphonyl halide (such as p-toluenesulphonyl chloride) in the presence of an acid acceptor, where L is a sulphonyloxy group. Compounds of formula (XX) can then be used as shown in Scheme V. Additionally, where L is halogen, they can be converted by reaction with a phosphine of formula Z(R$^5$)$_2$P, wherein R$^5$ is as defined above, into compounds of the invention of formula (I), where X is the group (R$^5$)$_2$P$^+$CHR$^2$Z$^-$. These compounds can then react successively with a base and a carbonyl compound of formula ZCOR$^1$, wherein Z and R$^1$ are as defined above, to give olefins of formula (XXIV).

Scheme VIII illustrates examples of intermediates of formula (VIII), shown in Scheme II, where W is any group that can be converted to ZX-, and Y is any group that can be converted to the methyl beta-methoxypropenoate group.

Compounds of formula (XXXI) can react with compounds of formula (XXXII) to give compounds of formula (XXXIII), using the general Ullmann coupling conditions described in detail for the reaction of compounds of formula (XI) and (XII) in Scheme II. The acids of formula (XXXIII) can be converted into methyl esters of formula (XXXIV) by reaction with methanol in the presence of acid (for example hydrochloric acid). Compounds of formula (XXXIV) can then be converted into methyl beta-methoxypropenoates of formula (XXVIII) by the methods described in detail in Scheme I.

Alternatively, the intermediates of formula (XXXIV) can be converted into intermediates of formulae (XXXVIII), (XXXV), (XXXVI), (XXXVII) and (III) using the methods described in Scheme VII for the conversion of the propenoates of formula (XXVIII) into compounds of formula (XXIII), (XX), (XXIX), (XXX) and (I). Compounds of formula (III) can be converted into compounds of formula (I) as shown in Scheme I.

Scheme VII

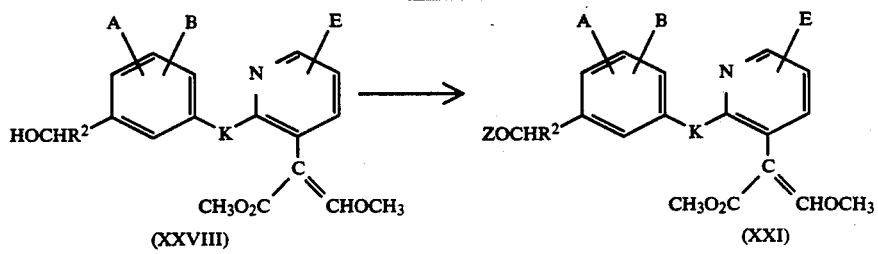

Scheme VII
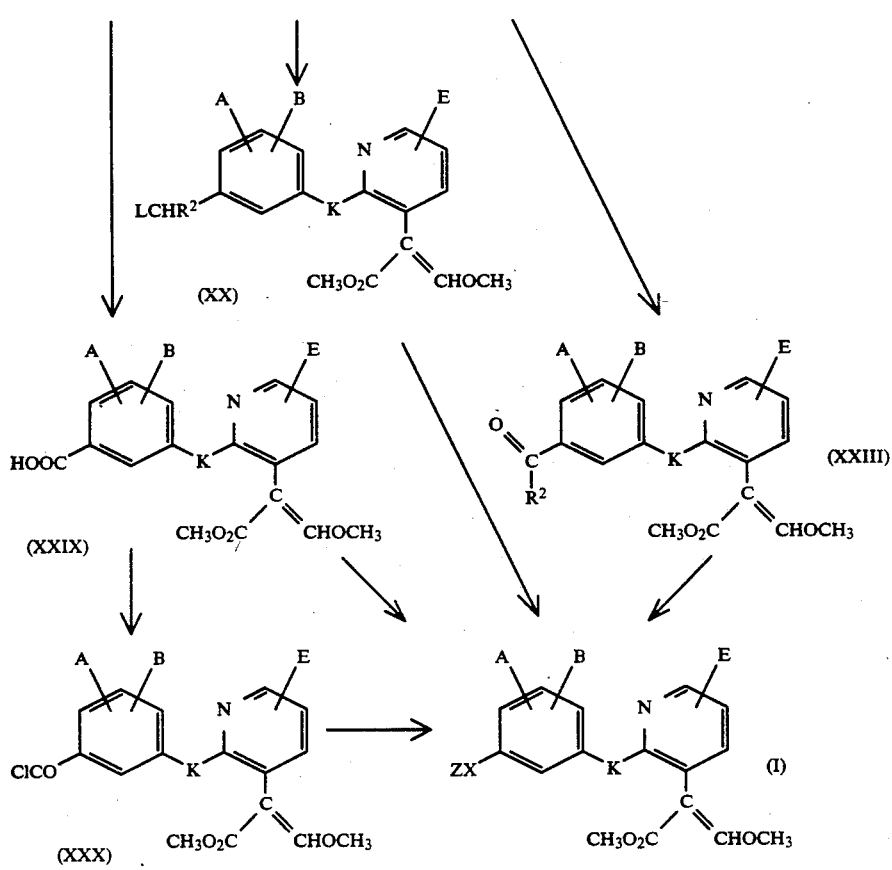
Scheme VIII
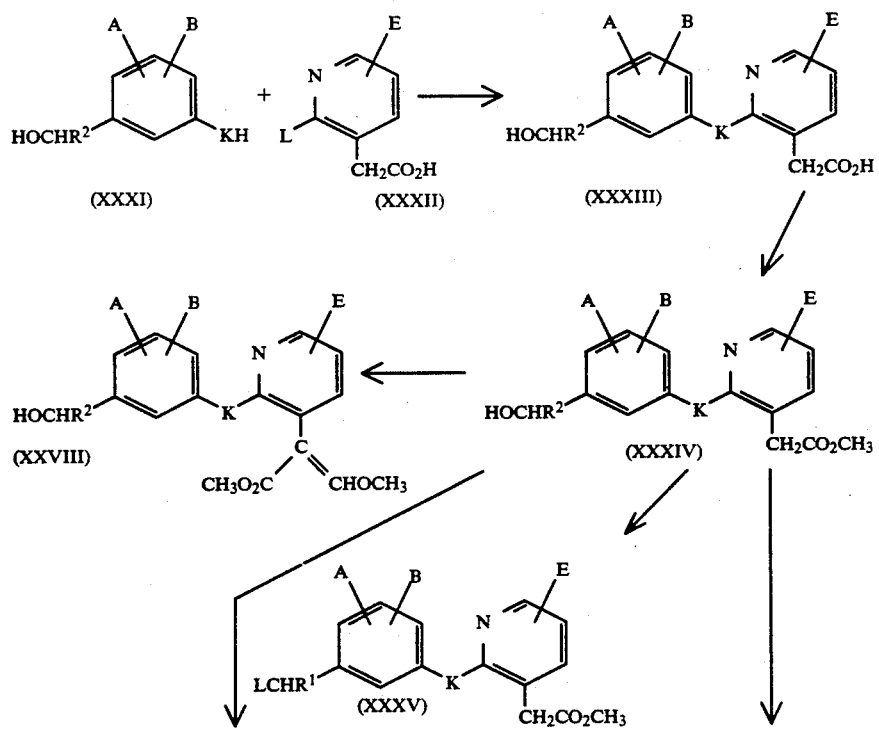

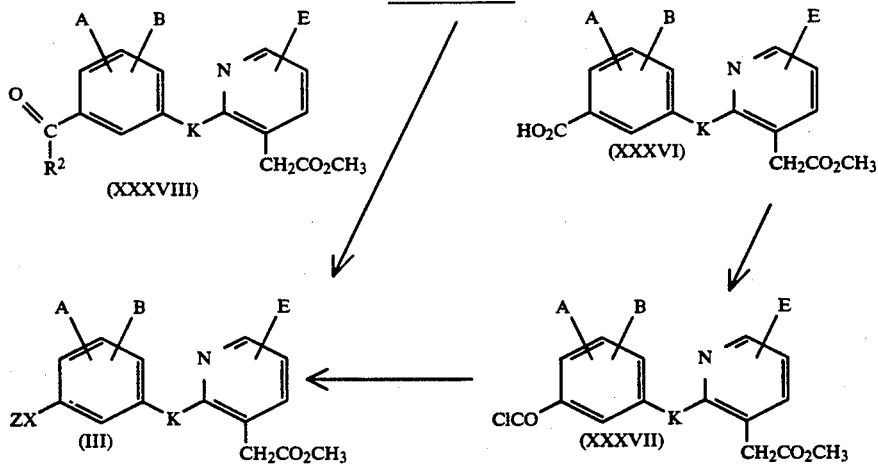

Scheme VIII

In a further aspect the invention provides processes as hereindescribed for preparing the compounds of formula (I). It also provides intermediate chemicals for formulae (II)–(VII) and (XIII)–(XXX), and (XXXIII)–(XXXVIII).

The compounds are active fungicides and may be used to control one or more of the following pathogens:

*Pyricularia oryzae* on rice.

*Puccinia recondita, Puccinia striiformis* and other rust on wheat, *Puccinia hordei, Puccinia striiformis* and other rusts on barley, and rusts on other hosts, e.g. coffee, pears, apples, peanuts, vegetables and ornamental plants.

*Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines. *Helminthosporium* spp., *Rhynchosporium* spp., *Septoria* spp., *Pseudocercosporella herpotrichoides* and *Gaeumannomyces graminis* on cereals. *Cercospora arachidicola* and *Cercosporidium personata* on peanuts and other *Cercospora* species on other hosts, for example, sugar beet, bananas, soya beans and rice.

*Botrytis cinerea* (grey mould) on tomatoes, strawberries, vegetables, vines and other hosts.

*Alternaria* species on vegetables (e.g. cucumber), oil seed rape, apples, tomatoes and other hosts.

*Venturia inaequalis* (scab) on applies.

*Plasmopara viticola* on vines.

Other downy mildews such as *Bremia lactucae* on lettuce, *Peronospora* spp. on soya beans, tobacco, onions and other hosts and *Pseudoperonospora humuli* on hops and *Pseudoperonospora cubensis* on cucurbits *Phytophthora infestans* on potatoes and tomatoes and other *Phytophthora* spp. on vegetables, strawberries, avocado, pepper, ornamentals, tobacco, coca and other hosts.

*Thanatephorus cucumeris* on rice and other *Rhizoctonia* species on various host such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloesporium musarum* and bananas and *Botrytis cinerea* on grapes).

Further some of the compounds may be active as seed dressings against *Fusarium* spp., *Septoria* spp., *Tilletia* spp., (bunt, a seed borne disease of wheat), *Ustilago* spp. *Helminthosporium* spp. on cereals, *Rhizoctonia solani* on cotton and *Pyricularia oryzae* on rice.

The compounds may have systemic movement in plants. Moreover, the compounds may be volatile enough to be active in the vapour phase against fungi on the plant.

The invention therefore provides a method of combating fungi, which comprises applying to a plant, to seed of a plant, or tot he locus of the plant or seed, an effective amount of compound as hereinbefore defined, or a composition containing the same.

The compounds may also be useful as industrial (as opposed to agricultural) fungicides, e.g. in the prevention of fungal attack on wood, hides, leather and especially paint films.

The compounds may be used directly for fungicidal purposes but are more conveniently formulated into compositions using a carrier or diluent. The invention thus provides a fungicidal composition comprising a compound of general formula (I) as hereinbefore defined, and a fungicidally acceptable carrier or diluent.

Used as fungicides, the compounds can be applied in a number of ways. For example they can be applied, formulated or unformulated, directly tot he foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be performed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be int he form of wettable powders of water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally controlling a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure int he presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium-, or phosphorus-containing fertilisers). Compositions comprising only granules of fertiliser incorporating, for example coated with, the compound are preferred. Such granules suitable contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95% suitable 10-85%, for example 25-60%, by weight of the active ingredient. After dilution to form aqueous preparations, suitable preparations may contain varying amounts of the active ingredient depending upon the intended purpose, but an aqueous preparation containing 0.00055 or 0.01% to 10% by weight of active ingredient may be used.

The compositions of this invention may contain other compounds having biological activity, e.g. compounds having similar or complementary fungicidal activity or which plant posses plant growth regulating, herbicidal or insecticidal activity.

A fungicidal compound which may be present in the composition of the invention may be one which is capable of combating ear disease of cereals (e.g. wheat) such as *Septoria, Gibberella* and *Helminthosporium* spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included int he composition of the invention are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl-aluminium, fenarimol, iprodione, prothiocarb, procymidone, vinclozolin, penconazole, myclobutanil, propamocarb, diniconazole, pyrazophos, ethirimol, ditalimfos, tridemorph, triforine, nuarimol, triazbutyl, guazatine, triacetate salt of 1,1'-iminodi(octamethylene)diguanidine, buthiobate, propiconazole, prochloraz, flutriafol, hexaconazole, (2RS, 5RS)-5-(2,4- dichlorophenyl)tetrahydro-5-(1H-1,2,4-triazol-1-ylmethyl)-2-furyl-2,2,2-trifluoroethyl ether, cyproconazole, terbuconazole, pyrrolnitrin, 1-[(2RS,4RS; 2RS, 4RS)-4-bromo-2-(2,4-dichlorophenyl)tetrahydrofur-furyl[-1H-1,2,4-triazole, 5-ethyl-5,8-dihydro-8-oxo(1,3)-dioxolo (4,5-g)quinoline-7-carboxylic acid, (RS)-1-aminopropylphosphonic acid, 3-(2,4-dichlorophenyl)-2-(1H-1,2,4-triazol-1-yl)quinazolin-4(3H)-one, fluzilazole, triadimefon, triadimenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, 4-chloro-N-(cyano(ethoxy)methyl)benzamide, pyroquilon, chlorbenzthiazone, neoasozin, polyoxin D, validamycin A, mepronil, flutolanil, pencycuron, diclomezine, phenazin oxide, nickel dimethyldithio-carbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, dichlone, chloroneb, binapacyl, nitrothalisopropyl, dodine, dithianon, fentin hydroxide, fentin acetate, tecnazene, quintozene, dicloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifo, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (e.g. GA$_3$, GA$_4$ or GA$_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acid (e.g. triiodobenzoic acid), morphactins (e.g. chlorfluoroecol), maleic hydrazide, glyphosate, glyphosine, long chain fatty alcohols and acids, dikegulac, paclobutrazol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2 -oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrates the invention. Throughout the Examples, the term 'ether' refers to diethyl ether, magnesium sulphate was used to dry solutions, and solutions were concentrated under reduced pressure. Reactions involving air- or water-sensitive intermediates were performed under an atmosphere of nitrogen and solvents were dried before use, where appropriate. Unless otherwise stated, chromatography was performed on a column of silica gel as the stationary phase. Where shown, infrared and n.m.r. data are selective; no attempt s made to list every absorption in all cases. $^1$H n.m.r. spectra were recorded using CDCl$_3$-solutions unless otherwise stated. The following abbreviations are used throughout:

| THF = | tetrahydrofuran | s = | singlet |
|---|---|---|---|
| DMF = | N,N-dimethylformamide | d = | doublet |
| n.m.r. = | nuclear magnetic resonance | t = | triplet |
| IR = | infrared | m = | multiplet |
| m.p. = | melting point | br = | broad |

This Example illustrates the preparation of (E)-methyl 2-[2-(3-phenoxyphenoxy)pyrid-3-yl]-3-methoxypropenoate (Compound No. 446 of Table I).

A mixture of potassium carbonate (5.53 g, 0.04 mol) and 3-phenoxyphenol (15 g, 0.08 mol) in DMF (60 ml) was heated at 80° C. with stirring for 30 minutes. 2-Chloro-3-cyanopyridine (11.08 g, 0.08 mol) and copper bronze (0.8 g) were added and the resulting mixture heated at reflux for 90 minutes. GC analysis indicated the formation of a single product (96%). The reaction mixture was cooled and filtered, and then poured into water (300 ml) and allowed to sand over the weekend. The yellow-brown oily precipitate was extracted into dichloromethane and dried. The dichloromethane solution was then filtered and evaporated to yield crude 2-(3-phenoxyphenoxy)-3-cyano-pyridine (36.2 g, contaminated with DMF) which was used in the next stage without further purification.

Crude 2-(3-phenoxyphenoxy(-3-cyanopyridine (15 g) was stirred with Raney nickel alloy (15 g, 50:50) in refluxing 75% formic acid (200 ml) for 2 hours. The reaction mixture was diluted with water and then extracted repeatedly with ether. The combined ether extracts were dried, filtered and evaporated to give an orange oil. Filtration through a plug of silica (eluent hexane-ether 1:1) afforded 2-(3-phenoxyphenoxy)-3-formylpyridine (3.03 g), infrared max. 1685 cm$^{-1}$.

To a stirred solution of the aldehyde (3.03 g, 0.01 mol) and methyl methylsulphinylmethyl sulphide (1.29 g, 0.01 mol) in dry THF (8 ml) at room temperature was added dropwise a solution of Triton B (2.5 ml, 40% in methanol). The resultant solution was heated to reflux for 1 hour, cooled and then diluted with water. Extraction with dichloromethane followed by drying and evaporation yielded a yellow oil which was dissolved in methanolic hydrogen chloride (100 ml) and allowed to stand overnight. The methanol was evaporated and the residue treated with saturated sodium bicarbonate solution and then extracted with dichloromethane. The combined organic extracts were dried, filtered and evaporated. The residue was chromatographed on silica gel (eluent hexane-ether, 1:1) to afford methyl 2-(3-phenoxyphenoxy)pyrid-3-ylacetate (1.35 g) as a pale yellow oil;

$^1$H NMR delta 3.68 (3H, s); 3.74 (2H, s); 6.74–6.88 (3H, m); 6.96–7.12 (4H, m); 7.24–7.40 (3H, m); 7.56–7.60 (1H, m); 8.06–8.12 (1H, m);

Infrared max. 1735 cm$^{-1}$.

A solution of methyl 2-(3-phenoxyphenoxy)pyrid-3-yl acetate (0.64 g, 0.0019 mol) and methyl formate (2.34 ml, 0.038 mol) in DMF (2 ml) was added dropwise over 15 minutes to a stirred suspension of petrol-washed sodium hydride (0.18 g, 0.0038 mol, 50% dispersion in oil) in DMF (10 ml). The temperature was kept below 10° C. during the addition. The reaction mixture effervesced vigorously and became yellow in colour. The temperature of the solution was allowed to rise to room temperature and stirring continued for 2 hours. The reaction mixture was poured into water (100 ml), neutralised with dilute hydrochloric acid and then extracted with ether (4×25 ml). The combined ether layers were washed with water and brine, and then dried and evaporated. The resulting yellow oil (0.69 g) was dissolved in DMF (10 ml) and then stirred with potassium carbonate (0.53 g) for 15 minutes. Dimethyl sulphate (0.17 ml) was then added in one portion and stirring continued for a further 4 hours. The reaction mixture was then diluted with water (100 ml) and extracted with ether (4×25). The combined extracts were washed with water and brine, dried, filtered and evaporated to afford an orange oil. Chromatography on silica gel (eluent 40–60 petrol-ether, 1:1) yielded a solid which on crystallisation from ethanol-petrol gave the title compound as a crystalline solid (0.32 g, 45%);

Melting point: 79°–81° C.;

$^1$H NMR delta 3.64 (3H, s); 3.84 (3H, s); 6.72–6.84 (3H, m); 7.00–7.12 (4H, m); 7.24–7.34 (3H, m); 7.52–7.60 (2H, m); 7.56 (1H, s); 8.08–8.14 (1H, m);

Infrared max. 1710, 1640 cm$^{-1}$.

EXAMPLE 2

This Example illustrates the preparation of (E)-methyl 2-[2-(3-benzyloxyphenoxy)pyridin-3-yl]-3-methoxypropenoate (Compound No. 23 of Table I).

3-Methoxyphenol (124 g) and anhydrous potassium carbonate (69 g) were heated together with stirring in dry DMF (500 ml) at 80° C. under an atmosphere of nitrogen. After 45 minutes, the greyish solution was cooled and 2-chloronicotinonitrile (138.5 g) and cooper bronze (10 g) were added (washed in with 100 ml DMF). The resulting brown reaction mixture was heated to 125°–130° C. After 2½ hours, the reaction mixture was cooled and filtered to remove excess copper bronze and undissolved solid material. The resulting solution was added to water (3 liters) and left to stand overnight. The resulting precipitate was filtered, washed with water then dissolved in ether. The ether solution was dried, filtered and evaporated to afford 2-(3-methoxyphenoxy)-3-cyanopyridine as an off-white solid (203.5 g, 90%).

Melting point: 66°–68° C.

Infrared max : 2232 cm$^{-1}$.

To a stirred solution of 2-(3-methoxyphenoxy)-3-cyanopyridine (5 g) dry THF (25 ml) at −70° C. under nitrogen was added dropwise diisobutylaluminum hydride (27.6 ml of a 1.0M solution in toluene) over 30 minutes. The mixture was stirred at −70° C. for a further 30 minutes then allowed to warm to room temperature. After 4 hours, GC analysis indicated 30% reaction. The reaction mixture was cooled to −70° C. and treated as before with a second batch of diisobutyl alumminium hydride (27.6 ml). After one hour at room temperature no starting material remained (GC analysis). Dilute hydrochloric acid (50 ml) was added very carefully (exotherm!). The resulting solution was stirred for a further 30 minutes and then partitioned with ether. The aqueous layer was further extracted (× 2) with ether. The ether combined layers were dried, filtered and evaporated to afford a yellow oil. Chromatography on silica gel (eluent dichloromethane) gave 2-(3-methoxyphenoxy)-3-pyridinecarboxaldehyde (1.7 g, 33%) as white crystals.

Melting point : 76°–78° C.

Infrared max. 1694 cm$^{-1}$ : $^1$H NMR delta 3.83 (3H, s); 6.75–6.84 (3H); 7.11–7.15 (1H); 7.33–7.38 (1H); 8.24–8.26 (1H); 8.35–8.38 (1H) ppm.

In a separate larger scale experiment 2-(3-methoxyphenoxy)-3-cyanopyridine (45 g) was converted (in 3 batches) into 2-(3-methoxyphenoxy)-3-pyridinecarboxaldehyde (34 g, 75%).

To a stirred solution of 2-(3-methoxyphenoxy)-3-pyridinecarboxaldehyde (8.07 g) and methyl methylsulphinylmethyl sulphide (6.78 ml) in dry THF (20 ml) at room temperature under nitrogen was added dropwise Triton B (14 mls, 40% solution in methanol). After heating to reflux for 1¼ hours GC analysis indicated the absence of starting material. The reaction mixture was cooled to room temperature and dichloromethane (450 ml) was added. The resultant solution was then dried, extracted with water (3×100 ml). The organic layer was then dried, filtered and evaporated to give an orange oil (22.88 g) which was used in the next stage without further purification. The orange oil was dissolved in methanolic hydrogen chloride (from (300 ml) methanol and (35 ml) acetyl chloride) stirred for 4 hours and left to stand at room temperature. After 2 days, the solvent was removed and the residue neutralised with saturated sodium bicarbonate solution. The product was extracted into ethyl acetate and the resulting solution dried, filtered and evaporated to afford crude methyl 2-(3-methoxyphenoxy)-3-pyridinyl acetate (15.83 g, 90% pure by GC).

Infrared max. 1740 cm$^{-1}$ : $^1$H NMR (CDCl$_3$) inter alia delta 3.71 (3H, s); 3.76 (2H); 3.95 (3H). In a separate experiment 2-(3-methoxyphenoxy)-3-pyridinecarboxaldehyde (33.03 g) was converted into methyl 2-(3-methoxyphenoxy)-3-pyridinylacetate (28 g, 71% overall).

Methyl 2-(3-methoxyphenoxy)-3-pyridinylacetate (27.2 g) was heated at 115° C. in 47% hydrobromic acid (249 ml) containing hexadecyltributylphosphonium bromide (5.6 g). After 3 hours, the solution was cooled and potassium carbonate added until the pH of the solution was ca. 6. The reaction mixture was extracted (× 5) with ethyl acetate. The organic extracts were dried, filtered and evaporated to give a pale orange solid. The solid was then treated with methanolic hydrogen chloride overnight (from methanol (500 ml) and acetyl chloride (50 ml)). The methanol was removed and the residue dissolved in water. The pH of the solution was adjusted to ca. pH6 with sodium bicarbonate and the solution extracted with ethyl acetate (× 3). The combined organic extracts were dried, filtered and evaporated. The resulting organge solid residue was re-dissolved in dichloromethane and filtered through a plug of silica (eluent ether dichloromethane). Evaporation afforded methyl 2-(3-hydroxyphenoxy)-3-pyridinylacetate as a pale yellow solid (13.28 g, 51%) which was used without further purification.

Methyl 2-(3-hydroxyphenoxy)-3-pyridinylacetate (0.8 g) and anhydrous potassium carbonate (0.21 g) were stirred together in DMF under nitrogen at 70° C. After 20 minutes benzyl bromide (1.06 g) was added together with copper bronze (cat.) and the reaction mixture heated to 100° C. for 3 hours. GC analysis indicated 50% reaction. A second equivalent of both potassium carbonate and benzyl bromide was added and heating continued at 100° C. for 2 hours. The reaction mixture was cooled to room temperature, filtered, diluted with water and extracted with ether (× 3). The ether extracts were combined, dried, filtered and evaporated to give a brown oil. Chromatography on silica gel (eluent petroleum ether - ether, 50:50) afforded methyl 2-(3-benzyloxyphenoxy)-3-pyridinylacetate as a light yellow solid (0.5 g, 46%).

Infrared max. 1735 cm$^{-1}$ : $^1$H NMR (CDCl$_3$) inter alia delta 3.70 (3H, s); 3.76 (2H, s); 5.04 (2H, s).

In a separate experiment, a further 0.3 g of product was obtained. The two samples were combined for the next stage.

A solution containing methyl formate (2.84 ml) and methyl 2-(3-benzyloxyphenoxy)-3-pyridinylacetate (0.8 g) in DMF (2 ml) was added dropwise to a stirred suspension of sodium hydride (0.22 g, 50% dispersion in oil, pre-washed with petroleum ether) in DMF (10 ml) (effervescence). The temperature was maintained below 10° C. during the course of the addition and then allowed to rise to room temperature. After stirring for a further 4 hours the reaction mixture was allowed to stand over the weekend. The reaction mixture was poured into water, just acidified with dilute hydrochloric acid and then extracted with ether (× 3). The combined ether extracts were dried, filtered and evaporated to give a yellow oil (0.86 g). The oil was dissolved in DMF (10 ml) and treated with potassium carbonate (0.64 g) and dimethyl sulphate (0.21 ml) at room temperature. After stirring for 4 hours GC analysis indicated complete reaction. Water (100 ml) was added and the resulting solution extracted with ether (3×25 ml). The combined ether extracts were washed with water then brine and dried. Filtration and evaporation gave an orange-brown oil. Chromatography on silica gel (eluent petroleum ether-ether, 50:50) affored the title compound as a white solid (0.2 g, 22%).

Melting point : 119°-122° C., mass spectrum m/e 391 (M+).

Infrared max. : 1705, 1640 cm$^{-1}$.

$^1$H NMR (CDCl$_3$) delta : 3.68 (3H, s); 3.84 (3H, s); 5.03 (2H, s); 6.66-6.80 (3H, m); 6.96-7.04 (1H, m); 7.20-7.42 (6H, m); 7.58 (1H, s); 7.60-7.62 (1H, m); 8.08-8.12 (1H, m).

EXAMPLE 3

This Example illustrates the preparation of (E)-methyl-2-[2-(3-((3-nitrobenzenesulphonyloxy)phenoxy)pyridin-3-yl]-3-methoxypropenoate (Compound No. 296 of Table I).

A solution containing methyl 2-(3-hydroxyphenoxy)-3-pyridinylacetate (1 g; prepared as described in Example 2) and methyl formate (4.68 ml) in DMF (5 ml) was added dropwise to a stirred suspension of sodium hydride (0.55 g, 50% dispersion in oil, pre-washed with petroleum ether) in DMF (10 ml). On completion of the reaction, the reaction mixture was worked up as before to afford crude methyl 2-[2-(3-(3-hydroxyphenoxy)-pyridin-3-yl]-3-hydroxypropenoate. The product was treated with potassium carbonate (0.31 g) and dimethyl sulphate (0.27 g) in DMF (10 ml) under the conditions described in Example 2 to give after standard work-up an oil. Chromatography on silica gel (eluent petroleum ether - ether, 50:50) gave (E)-methyl 2-[2-(3-hydroxyphenoxy)pyridin-3-yl]-3-methoxypropenoate as a white solid (0.35 g, 31%).

Melting point : 163°-165° C.; mass spectrum m/e 301 (M+).

Infrared max. 1665, 1663 cm$^{-1}$ : $^1$H NMR (CDCl$_3$) delta 3.68 (3H, s); 3.86 (3H, s); 6.48 (1H); 6.54-6.6 (3H); 7.00-7.06 (1H); 7.12-7.20 (1H); 7.58 (1H, s); 7.60-7.64 (1H); 8.08-8.12 (1H) ppm.

(E)-Methyl 2-[2-(3-hydroxyphenoxy)pyridin-3-yl]-3-methoxypropenoate (0.1 g, prepared as described above) was stirred with 3-nitrobenzenesulphonyl chloride (0.074 g) and triethylamine (0.074 ml) in dry dichloromethane (3 ml) at room temperature. After one hour the reaction mixture was applied directly onto a silica gel column. Elution with petroleum ether - ether (50:50) afforded the title compound as a white foamy solid (0.101 g, 63%).

Melting point : 49°-51° C.; mass spectrum m/e 486 (M+).

Infrared max. 1710, 1638 cm$^{-1}$ : $^1$H NMR (CDCl$_3$) delta 3.66 (3H,s), 3.85 (3H,s); 6.77-6.83 (2H); 7.00-7.09 (2H); 7.29-7.31 (1H); 7.57 (1H, s); 7.60-7.62 (1H); 7.71-7.78 (1H); 8.03-8.08 (1H) ppm.

EXAMPLE 4

This Example illustrates the preparation of (E)-methyl 2-[2-(3-((4-nitrophenoxy)phenoxy)pyridin-3-yl]-3-methoxypropenoate (Compound No. 133 of Table I).

(E)-Methyl 2-[2-(3-hydroxyphenoxy)pyridin-3-yl]-3-methoxypropenoate (0.3 g; prepared as described in Example 3) and potassium carbonate (0.069 g) were heated together in DMF (5 ml) at 70° C. After 20 minutes, 4-fluoronitrobenzene (0.141 g) and copper-bronze (cat.) were added and the resulting mixture heated at 130° C. for 2 hours. GC analysis indicated the absence of starting material. The reaction mixture was filtered and then poured into water (70 ml). The resulting mixture was extracted with ether (× 3). The combined ether extracts were dried, filtered and evaporated to give an orange oil. Chromatography on silica gel afforded the title compound as a white crystalline solid (0.266 g, 64%).

Melting point : 102°-103° C.; mass spectrum m/e 422(M+).

Infrared max. 1700, 1626 cm$^{-1}$ : $^1$H NMR (CDCl$_3$) delta 3.64 (3H, s); 3.85 (3H, s); 6.80-6.88 (2H); 6.94-7.10 (4H); 7.36-7.42 (1H); 7.59 (1H, s); 7.60-7.64 (1H); 8.10-8.12 (1H); 8.16-8.22 (2H).

EXAMPLE 5

This Example illustrates the preparation of (E)-methyl 2-[2-(3-pyrimidin-2-yloxy)phenoxy)pyridin-3-yl]-3-methoxypropenoate (Compound No. 22 of Table II).

(E)-Methyl 2-[2-(3-hydroxyphenoxy)pyridin-3-yl]-3-methoxypropenoate (0.67 g; prepared as described in Example 3) was heated at 80° C. with potassium carbonate (0.154 g) in DMF (10 ml) under an atmosphere of nitrogen. After 20 minutes 2-chloropyrimidine (0.253 g) and copper-bronze (cat.) were added and the resultant mixture heated at 130° C. with stirring for 2½ hours. GC analysis indicated the completion of the reaction. The reaction mixture was cooled, filtered and then poured into water. The aqueous phase was then extracted with ether (× 3). The combined ether layers were dried, filtered and evaporated to give a yellowish solid. Chromatography on silica gel (eluent ether - ether acetate, 2:1) gave the title compound as a white solid (0.308 g, 37%).

Melting point : 151°-153° C.; mass spectrum m/e 379(M+).

Infrared max. 1695, 1635 cm$^{-1}$ : $^1$H NMR (CDCl$_3$) delta 3.68 (3H,s ); 3.85 (3H, s); 6.94-7.06 (5H); 7.38-7.43 (1H); 7.57 (1H, s); 7.62-7.66 (1H); 8.11-8.15 (1H); 8.53-8.57 (2H) ppm.

EXAMPLE 6

This Example illustrates the preparation of (E)-methyl 2-[2-(3-phenoxymethylphenoxy)pyridin-3-yl]-3-methoxypropenoate (Compound No. 21 of Table I).

A mixture of 2-chloro-3-pyridinecarboxaldehyde (10.0 g), 3-hydroxybenzyl alcohol (8.76 g); anhydrous potassium carbonate (4.88 g) in DMF (70 ml) was heated to reflux. After 3 hours, GC analysis showed that all of the aldehyde had been consumed. The reaction mixture was cooled and filtered and then poured into water. The resultant mixture was extracted with ether (× 3) and the combined ether layers washed once with dilute sodium hydroxide solution. The ether solution was then dried, filtered and evaporated to give a pale orange oil which crystallised on standing (9.13 g). To a solution of this product (6.24 g) and methyl methylsulphinylmethyl sulphide (3.38 g) in THF at room temperature under nitrogen was added dropwise Triton B (8 ml, 40% solution in methanol). After heating at reflux for 4 hours, the reaction mixture was cooled at room temperature and dichloromethane (300 ml) was added. The resultant solution was extracted with water (× 3). The dichloromethane layer was dried, filtered and evaporated to give a dark orange oil (8.5 g) which was used directly in the next stage.

The dark organge oil (8.5 g, crude) was dissolved in methanolic hydrogen chloride (from methanol (150 ml) and acetyl chloride (15 ml)), stirred for 3 hours and then left to stand over the weekend. The methanol was removed by evaporation and a saturated aqueous solution of sodium bicarbonate was added. The mixture was extracted with ethyl acetate (× 3) and the combined organic layers dried, filtered and evaporated to give a yellow oil. The oil was filtered through a plug of silica (eluent dichloromethane then ether).

Evaporation of the solvent afforded methyl 2-(3-hydroxymethylphenoxy)-3-pyridinylacetate as a pale orange oil (4.04 g, 88% pure by GC).

Infrared max. 3400, 1737 cm$^{-1}$.

The product was used in the next stage without further purification.

A solution of methyl 2-(3-hydroxymethylphenoxy)-3-pyridinylacetate (0.6 g) and triethylamine (0.45 ml) in dichloromethane (2 ml) was added dropwise over 20 minutes to a stirred solution of mesyl chloride (0.26 ml) in dichloromethane (6 ml) at ca. 5° C. The mixture was stirred at 5° C. for 30 minutes, warmed to room temperature and then allowed to stand over the weekend. GC analysis of an aliquot indicated complete reaction. The reaction mixture was stirred with brine for 30 minutes and then the organic layer was dried, filtered and evaporated to give methyl 2-(3-chloromethylphenoxy)-3-pyridinylacetate as a pale yellow oil (0.55 g) which was used directly.

Infrared max. 1738 cm$^{-1}$; mass spectrum m/e 291 (M+).

$^1$H NMR (CDCl$_3$) : inter alia delta 3.69 (3H, s); 3.77 (2H, s); 4.60 (2H, s).

Phenol (0.16 g) and potassium carbonate (0.12 g) were stirred together in DMF (6 ml) under nitrogen at room temperature. After 20 minutes, a solution of methyl 2-(3-chloromethylphenoxy)-3-pyridinylacetate (0.5 g) in DMF was added and stirring continued. Copper-bronze (cat.) was added and the reaction mixture heated at 100° C. for a total of 5 hours. GC analysis indicated complete reaction. The reaction mixture was cooled and filtered, and then poured into water (50 ml). The aqueous mixture was extracted with ether (× 3) and the combined extracts washed with dilute sodium hydroxide solution. The ether solution was the dried, filtered and evaporated to give methyl 2-(3-phenoxymethylphenoxy)-3-pyridinylacetate as a yellow oil (0.35 g, 59%), mass spectrum m/e 349 (M+); $^1$H NMR (CDCl$_3$) inter alia delta 3.69 (3H, s); 3.76 (2H, s); 5.07 (2H, s) ppm, contained with traces of DMF. In a separate experiment, the chloromethyl compound (2.73 g, prepared as above) yielded a further 2.00 g of methyl 2-(3-phenoxymethylphenoxy)-3-pyridinylacetate.

A solution of methyl 2-(3-phenoxymethylphenoxy)-3-pyridinylacetate (2.35 g) and methyl formate (6.2 ml) in DMF was added to a suspension of sodium hydride (0.64 g, 50% dispersion in oil, pre-washed with petroleum ether) in DMF (25 ml) under the same conditions described in the final stage of Example 1. Standard work-up yielded crude methyl 2-[2-(3-phenoxymethylphenoxy)pyridin-3-yl]-3-hydroxpropenoate which was treated directly with potassium carbonate (1.85 g) and dimethylsulphate (0.63 ml) in DMF (17 ml). Standard work-up and chromatography on silica gel (eluent petroleum ether-ether, 50:50) afforded the title compound as a white gum (0.53 g), 1638 cm$^{-1}$; $^1$H NMR as in Table V.

EXAMPLE 7

This Example illustrates the preparation of (E)-methyl 2-[2-(3-(2-methoxyphenoxy)phenoxy)pyridin-3-yl]-3-methoxypropenoate (Compound No. 128 of Table I).

To an ice-cold stirred suspension of petrol-washed sodium hydride (1.04 g, 50% dispersion in oil, 22 mmol) in DMF (16 ml) was added a solution of methyl 2-chloropyrid-3-ylacetate (2 g, 11 mmol) and methyl formate (12.95 g, 0.22 mol) in DMF (8 ml). The reaction mixture was allowed to warm to room temperature and stirring continued until tlc analysis showed that no starting material remained (ca. 3 hours). The reaction mixture was poured into water and then acidified with dilute hydrochloric acid. The solution was extracted repeatedly with ether and the combined extracts dried, filtered and evaporated. The residue was redissolved in DMF and then treated with dimethyl sulphate (1.32 g, 10.5 mmol) and anhydrous potassium carbonate (1.52 g, 11 mmol) at room temperature.

The reaction mixture was stirred for 2 hours, diluted with water and then repeatedly extracted with ether. The combined ether extracts were dried, filtered and evaporated to afford a yellow oil. Chromatography on silica (eluent petrol-ether, 50:50) gave (E)-methyl 2-(2-chloropyrid-3-yl)-3-methoxypropenoate as a white waxy solid (0.9 g, 36%).

Melting point : 39°-40° C.

Infrared max. : 1711, 1638 cm$^{-1}$.

$^1$H NMR delta : 3.74 (3H, s), 3.89 (3H, s), 7.21-7.26 (1H), 7.55-7.57 (1H), 7.60 (1H, s), 8.32-8.36 (1H).

(E)-Methyl 2-(2-chloropyridin-3-yl)-3-methoxypropenoate (0.227 g), 3-(2-methoxyphenoxy)phenol (0.255 g), anhydrous potassium carbonate (0.069 g), copper-bronze (cat.) and copper (I) chloride (cat.) were heated together at ca. 170° C. for 3 hours under nitrogen. The reaction mixture was cooled and then diluted with a small amount of dichloromethane. The resulting mixture was applied directly to a column of silica gel and chromatographed (eluent petroleum ether-ether, 1:1) to afford the title compound as a pale brown oil (0.023 g, 6%), mass spectrum m/e 407 (M+) $^1$H NMR (CDCl$_3$) as in Table V.

EXAMPLE 8

This Example illustrates the preparation of (E)-methyl 2-[2-(3-(alpha-hydroxybenzylphenoxy)pyridin-3-yl]-3-methoxypropenoate (Compound No. 380 of Table I).

To a stirred suspension of sodium hydride (1.056 g, 50% dispersion in oil, pre-washed with petroleum ether) in dry DMF (15 ml) at 0°-5° C. was added dropwise over 5 minutes a solution containing methyl 2-(3-hydroxymethylphenoxy)pyridin-3-ylacetate (2.0 g) and methyl formate (9 ml) in DMF (effervescence). After the addition was complete, the reaction mixture was allowed to warm to room temperature. After stirring for a further 3 hours, the reaction mixture was carefully poured into water, neutralised with 2N hydrochloric acid and then extracted thoroughly with ether ($\times$ 6). The combined ether layers were dried, filtered and evaporated to afford a crude residue which was used without further purification. The residue was dissolved in DMF (10 ml) and then treated with potassium carbonate (0.60 g) and dimethyl sulphate (0.64 g). Standard work-up and chromatography on silica gel (eluent petroleum ether-ether, 1:1) afforded (E)-methyl 2-[2-(3hydroxymethylphenoxy)pyridin-3-yl]-3-methoxypropenoate (0.35 g, 15%); mass spectrum m/e 315 (M+).

Infrared max. : 3396 (br.), 1708, 1638 cm$^{-1}$.

$^1$H NMR (CDCl$_3$) delta : 1.63 (br. 0—H); 3.69 (3H, s); 3.85 (3H, s); 4.69 (2H, s); 6.98–7.05 (2H, m); 7.09–7.17 (2H, m); 7.31–7.37 (1H, m); 7.57 (1H, s); 7.61–7.63 (1H, m); 8.07–8.11 (1H, m) ppm.

(This compound can be converted to (E)-methyl 2-[2-(3-chloromethyl)pyridin-3-yl]-3-methoxypropenoate by treatment with mesyl chloride and triethylamine as described for methyl 2-(3-chloromethylphenoxy)-pyridin-3-ylacetate in Example 6).

To a stirred solution of (E)-methyl 2-[2-(3-hydroxymethylphenoxy)pyridin-3-yl]-3-methoxypropenoate (0.250 g) in dichloromethane (5 ml) at room temperature was added pyridinium dichromate (0.414 g). After stirring for 3 hours, GC analysis of an aliquot indicated the absence of starting material. Water was added and stirring continued for 10 minutes. The reaction mixture was filtered (filter washed through with water (5 ml) and dichloromethane (5 ml)) and then further diluted with dichloromethane (5 ml). The organic layer was separated and the aqueous phase further extracted with dichloromethane ($\times$ 3). The combined organic layers were dried, filtered and evaporated to give a dark yellow oil. Chromatography on silica gel (eluent ether-petroleum ether, 7:3) afforded (E)-methyl 2-[2-(3-formylphenoxy)pyridin-3-yl]-3-methoxypropenoate (0.136 g, 55%) as a white solid.

Melting point : 84°-86° C.
Infrared max. : 1705, 1698, 1633 cm$^{-1}$.
$^1$H NMR (CDCl$_3$) delta : 3.64 (3H, s); 3.85 (3H, s); 7.04–7.08 (1H, m); 7.36–7.40 (1H, m); 7.59 (1H, s); 7.50–7.70 (4H, m); 8.09–8.11 (1H, m); 10.00 (1H, s).

To a stirred solution of (E)-methyl 2-[2-(3-formylphenoxy)pyridin-3-yl]-3-methoxypropenoate (0.115 g) in ether (3 ml, containing a few drops of THF) under nitrogen at $-5°$ to $-10°$ C. was added dropwise over 15 minutes phenylmagnesium bromide (1 equiv. in 2 ml ether). After a further 20 minutes, GC analysis of an aliquot indicated the presence of starting material (34%). A further 0.2 equivalents of phenylmagnesium bromide was added and stirring continued for 10 minutes. GC analysis of an aliquot showed the absence of starting material. The reaction mixture was poured into ice and a few drops of 15% sulphuric acid were added. The ether layer was separated and the aqueous residue extracted with ether ($\times$ 2). The combined organic extracts were dried, filtered and evaporated to give a yellow oil. Chromatography on silica gel (eluent ether-petroleum ether, 6:4) gave the title compound as the major product (white oil, 0.059 g, 40%); mass spectrum m/e 391 (M+).

Infrared max. : 3420, 1707, 1637 cm$^{-1}$.

$^1$H NMR (CDCl$_3$) delta : 2.35 (1H, br. s); 3.63 (3H, s); 3.81 (3H, s); 5.83 (1H, s); 6.96–7.40 (10H, m); 7.55 (1H, s); 7.58–7.62 (1H, m); 8.06–8.09 (1H, m) ppm.

The following are examples of compositions suitable for agricultural and horticultural purposes which can be formulated from the compounds of the invention. Such compositions form another aspect of the invention. Percentages are by weight.

EXAMPLE 9

An emulsifiable concentrate is made up by mixing and stirring the ingredients until all are dissolved.

| Compound No. 446 of Table I | 10% |
| Benzyl alcohol | 30% |
| Calcium dodecylbenzenesulphonate | 5% |
| Nonylphenolethoxylate (13 mole ethylene oxide) | 10% |
| Alkyl benzenes | 45% |

EXAMPLE 10

The active ingredient is dissolved in methylene dichloride and the resultant liquid sprayed on to the granules of attapulgite clay. The solvent is then allowed to evaporate to produce a granular composition.

| Compound No. 446 of Table I | 5% |
| Attapulgite granules | 95% |

EXAMPLE 11

A composition suitable for use as a seed dressing is prepared by grinding and mixing the three ingredients.

| Compound No. 446 of Table I | 50% |
| Mineral oil | 2% |
| China clay | 48% |

EXAMPLE 12

A dustable powder is prepared by grinding and mixing the active ingredient with talc.

| | |
|---|---|
| Compound No. 446 of Table I | 5% |
| Talc | 95% |

EXAMPLE 13

A suspension concentrate is prepared by ball milling the ingredients to form an aqueous suspension of the ground mixture with water.

| | |
|---|---|
| Compound No. 446 of Table I | 40% |
| Sodium lignosulphonate | 10% |
| Bentonite clay | 1% |
| Water | 49% |

This formulation can be used as a spray by diluting into water or applied directly to seed.

EXAMPLE 14

A wettable powder formulation is made by mixing together and grinding the ingredients until all are thoroughly mixed.

| | |
|---|---|
| Compound No. 446 of Table I | 25% |
| Sodium lauryl sulphate | 2% |
| Sodium lignosulphonate | 5% |
| Silica | 25% |
| China clay | 43% |

EXAMPLE 15

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubate until the disease was ready for assessment. The period between inoculation and assessment varied from four to fourteen days according to the disease and environment.

The disease control was recorded by the following grading:

TABLE VI

| COMPOUND NO. | TABLE NO. | PUCCINIA RECONDITA (WHEAT) | ERYSIPHE GRAMINIS HORDEI (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS (TOMATO) |
|---|---|---|---|---|---|---|---|---|
| 21  | I  | 4  | 4  | 4  | 4  | 4  | 4  | 2 |
| 23  | I  | 4  | 4  | 4  | 3  | 4  | 4  | 4 |
| 119 | I  | 4  | 3  | 4  | 3  | 4  | 4  | 4 |
| 128 | I  | 4a | 2a | 4a | 3a | 4a | 4a | 3a |
| 131 | I  | 4  | 4  | 4  | 4  | 4  | 4  | 4 |
| 133 | I  | 4  | 3  | 4  | 2  | 3  | 4  | 0 |
| 134 | I  | 4a | 4a | 4a | 4a | 4a | 4a | 4a |
| 212 | I  | 4  | 3  | 4  | 4  | 4  | 4  | 4 |
| 296 | I  | 3a | 0a | 2a | 1a | 0a | 4a | 3a |
| 376 | I  | 3  | 4  | 4  | 4  | 4  | 4  | 2 |
| 381 | I  | 3  | 0  | 4  | 0  | 0  | 4  | 2 |
| 446 | I  | 4  | 4  | 4  | 4  | 3  | 4  | 4 |
| 447 | I  | 4  | 3  | 3  | 0  | 4  | 4  | 4 |
| 22  | II | 4  | 4  | 4  | 4  | 3  | 4  | 0 |
| 89  | II | 4  | 4  | 3  | —  | 3  | 4  | 4 |
| 97  | II | 3  | 4  | 4  |    | 2  | 4  | 3 |
| 106 | II | 4  | 4  | 4  | —  | 4  | 4  | 4 |
| 320 | II | 3  | 4  | 4  |    | 3  | 4  | 3 | a = 25 ppm foliar spray only
— = no result

We claim:

1. A fungicidal compound of the formula (I):

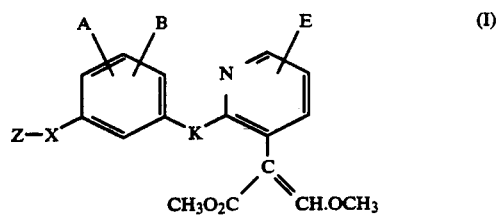

or a stereoisomer thereof, wherein A, B and E, which are the same or different, are H, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; K is oxygen or sulphur; X is O; and Z is aryl substituted with one or more of halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)alkyl, $C_{1-4}$alkoxy($C_{1-4}$)alkyl, $C_{3-6}$ cycloalkyl, $C_{3-6}$ cycloalkyl($C_{1-4}$)alkyl, aryl, pyridinyl or pyrimidinyl, aryloxy, aryl($C_{1-4}$)alkyl, aryl($C_{1-4}$)alkyl in which the alkyl moiety is substituted with hydroxy, pyrimidinyl($C_{1-4}$)alkyl or pyridinyl($C_{1-4}$)alkyl, aryl($C_{2-4}$)alkenyl, pyrimidinyl($C_{2-4}$)alkenyl or pyridinyl($C_{2-4}$)alkenyl, aryl($C_{1-4}$)alkoxy, pyrimidinyl($C_{1-4}$)alkoxy or pyridinyl($C_{1-4}$)alkoxy, aryloxy($C_{1-4}$)alkyl, pyrimidinyloxy($C_{1-4}$)alkyl or pyridinyloxy($C_{2-4}$)alkyl, carbacyloxy, cyano, thiocyanato, nitro, —NR'R", —NHCOR', —NHCONR'R", —CONR'R", —COOR', —OSO$_2$R', —SO$_2$R', —COR', —CR=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, or phenyl or benzyl substituted with halogen, $C_{1-4}$ alkyl or $C_{1-4}$ alkoxy; the aryl or pyrimidinyl or pyridinyl rings of any of the foregoing substituents being optionally substituted with one or more of halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" have the meanings given above provided that Z is not phenyl substituted only with $C_{1-4}$ alkyl.

2. A fungicidal compound of the formula (Ia):

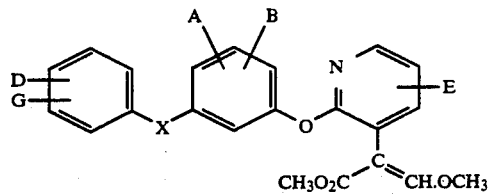

wherein X is O; A is H, hydroxy, halo, $C_{1-4}$ alkyl, $C_{1-4}$ alkoxy, trifluoromethyl, nitro, cyano, acetyl or phenoxy; B and E are H or halo; D is hydroxy, halo, $C_{1-4}$ alkoxy, nitro, cyano, halo($C_{1-4}$)alkyl, halo($C_{1-4}$)alkoxy, phenyl, phenoxy, NHCOR$^6$, NHSO$_2$R$^6$, NR$^7$R$^8$, CO$_2$R$^7$, wherein R$^6$ is $C_{1-4}$ alkyl or phenyl and R$^7$ and R$^8$ are independently H or $C_{1-4}$ alkyl, or CH$_3$O$_2$C.C=CH.OCH$_3$; and G is H, halo, $C_{1-4}$ alkyl, $C_{1-4}$ alkoxy or nitro; or D and G, when they are adjacent, join to form a benzene or pyridine ring.

3. A compound according to claim 2 wherein X is O; D is halo, $C_{1-4}$ alkoxy, nitro, cyano or amino; and A, B, E and G are all H.

4. A fungicidal composition comprising a fungicidally effective amount of a compound according to claim 1 and a fungicidally acceptable carrier or diluent therefor.

5. A method of combating fungi which comprises applying to plants, to the seeds of plants or to the locus of the plants or seeds, a compound according to claim 1 or a composition according to claim 1.

* * * * *